(12) United States Patent
Yamaji

(10) Patent No.: US 11,191,480 B2
(45) Date of Patent: Dec. 7, 2021

(54) DEVICE FOR BIORHYTHM DETECTION, METHOD FOR BIORHYTHM DETECTION, AND RECORDING MEDIUM RECORDING PROGRAM FOR BIORHYTHM DETECTION

(71) Applicant: FUJITSU LIMITED, Kawasaki (JP)

(72) Inventor: Takayuki Yamaji, Yokahama (JP)

(73) Assignee: FUJITSU LIMITED, Kawasaki (JP)

(*) Notice: Subject to any disclaimer, the term of this patent is extended or adjusted under 35 U.S.C. 154(b) by 409 days.

(21) Appl. No.: 16/209,240

(22) Filed: Dec. 4, 2018

(65) Prior Publication Data
US 2019/0110742 A1 Apr. 18, 2019

Related U.S. Application Data

(63) Continuation of application No. PCT/JP2016/069036, filed on Jun. 27, 2016.

(51) Int. Cl.
*A61B 5/00* (2006.01)
*A61B 5/11* (2006.01)

(52) U.S. Cl.
CPC .............. *A61B 5/4857* (2013.01); *A61B 5/11* (2013.01); *A61B 5/1118* (2013.01); *A61B 5/725* (2013.01); *A61B 5/7425* (2013.01); *A61B 5/7257* (2013.01); *A61B 2560/0475* (2013.01); *A61B 2562/0219* (2013.01)

(58) Field of Classification Search
CPC ....... A61B 5/4857; A61B 5/11; A61B 5/1118; A61B 5/725; A61B 5/7425; A61B 5/7257; A61B 2560/0475; A61B 2562/0219
See application file for complete search history.

(56) References Cited

U.S. PATENT DOCUMENTS 4,883,353 A * 11/1989 Hausman ........... A61B 5/02433
356/41
2005/0075553 A1 4/2005 Sakai et al.
(Continued)

FOREIGN PATENT DOCUMENTS

JP 4-367653 A 12/1992
JP 6-189914 A 7/1994
(Continued)

OTHER PUBLICATIONS

Extended (Supplementary) European Search Report dated May 28, 2019, issued in counterpart EP application No. 16907228.7. (7 pages).

(Continued)

*Primary Examiner* — Eric F Winakur
*Assistant Examiner* — Abid A Mustansir
(74) *Attorney, Agent, or Firm* — Westerman, Hattori, Daniels & Adrian, LLP

(57) ABSTRACT

A device for biorhythm detection, includes: a memory; and a processor coupled to the memory and configured to perform operations of: acquiring activity amount data indicating an amount of activity of a test subject which is measured by an activity amount meter configured to measure the amount of activity of the test subject; and detecting, as a frequency derived from a biorhythm of the test subject, a frequency that indicates peak power in a result which is obtained through frequency analysis of a first time waveform of the activity amount data.

17 Claims, 22 Drawing Sheets

(56) References Cited

U.S. PATENT DOCUMENTS

| | | | |
|---|---|---|---|
| 2006/0224047 A1* | 10/2006 | Suzuki | A61B 5/4806 |
| | | | 600/300 |
| 2009/0149778 A1 | 6/2009 | Naujokat et al. | |
| 2012/0296175 A1 | 11/2012 | Poh et al. | |
| 2013/0178720 A1* | 7/2013 | Sazuka | A61B 5/02055 |
| | | | 600/301 |
| 2014/0194756 A1 | 7/2014 | Sazuka | |
| 2017/0231562 A1* | 8/2017 | Park | A61B 5/021 |
| | | | 600/485 |

FOREIGN PATENT DOCUMENTS

| | | |
|---|---|---|
| JP | 6-217946 A | 8/1994 |
| JP | 9-313492 A | 12/1997 |
| JP | 2000-166877 A | 6/2000 |
| JP | 2004-283523 A | 10/2004 |
| JP | 2005-198829 A | 7/2005 |
| JP | 2012-239799 A | 12/2012 |
| JP | 2014-147595 A | 8/2014 |
| JP | 2015-228911 A | 12/2015 |
| WO | 2009/073811 A2 | 6/2009 |
| WO | 2012/011318 A1 | 1/2012 |
| WO | 2014/084928 A1 | 6/2014 |

OTHER PUBLICATIONS

International Search Report dated Sep. 20, 2016, issued in counterpart International Application No. PCT/JP2016/069036 (2 pages).

* cited by examiner

FIG. 14

| DAY | FREQUENCY [Hz] | CALCULATED TIME | TIME DIFFERENCE WITH RESPECT TO 24 HOURS |
|---|---|---|---|
| 1 | 1.28571429 | 18.66667 | -5.333333333 |
| 2 | 0.71428571 | 33.6 | 9.6 |
| 3 | 0.78571429 | 30.54545 | 6.545454545 |
| 4 | 1.5 | 16 | -8 |
| 5 | 0.89285714 | 26.88 | 2.88 |
| 6 | 0.85714286 | 28 | 4 |
| 7 | 1.21428571 | 19.76471 | -4.235294118 |
|  | Ave. | 24.77955 | 0.779546728 |

FIG. 18

| DATE | TIME |
|---|---|
| JUNE 1 | -5 |
| JUNE 2 | 9.6 |
| JUNE 3 | 6.5 |
| JUNE 4 | -8 |
| JUNE 5 | 2.8 |
| JUNE 6 | 4 |
| JUNE 7 | -4.2 |

DEVICE FOR BIORHYTHM DETECTION, METHOD FOR BIORHYTHM DETECTION, AND RECORDING MEDIUM RECORDING PROGRAM FOR BIORHYTHM DETECTION

CROSS-REFERENCE TO RELATED APPLICATION

This application is a continuation application of International Application PCT/JP2016/069036 filed on Jun. 27, 2016 and designated the U.S., the entire contents of which are incorporated herein by reference.

FIELD

The embodiments discussed herein are related to a device for biorhythm detection, a method for biorhythm detection, and a recording medium recording a program for biorhythm detection.

BACKGROUND

A physiological rhythm (may also be referred to as "biorhythm") of a biological body is detected or estimated. For example, the rectal temperature of a test subject is measured for 24 or more hours to estimate a biorhythm curve and the heartbeat of a test subject is measured for 24 or more hours to estimate a biorhythm curve.

Related art is disclosed, PTL 1: Japanese Laid-open Patent Publication No. 6-189914, PTL 2: Japanese Laid-open Patent Publication No. 6-217946, PTL 3: Japanese Laid-open Patent Publication No. 2005-198829, PTL 4: Japanese Laid-open Patent Publication No. 2012-239799, PTL 5: International Publication Pamphlet No. WO 2012/011318, PTL 6: Japanese Laid-open Patent Publication No. 9-313492, and PTL 7: Japanese Laid-open Patent Publication No. 2015-228911.

SUMMARY

According to one aspect of the embodiments, a device for biorhythm detection, includes: a memory; and a processor coupled to the memory and configured to perform operations of: acquiring activity amount data indicating an amount of activity of a test subject which is measured by an activity amount meter configured to measure the amount of activity of the test subject; and detecting, as a frequency derived from a biorhythm of the test subject, a frequency that indicates peak power in a result which is obtained through frequency analysis of a first time waveform of the activity amount data.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 14 is a table illustrating an example of a biorhythm (frequency f) of a test subject for each day, a time that is calculated from the biorhythm, and a time difference with respect to 24 hours, which are obtained from the activity amount data of seven days exemplified in FIGS. 7 to 13.

FIG. 18 is a table illustrating an example of a visual display mode of data with regard to a circadian rhythm.

DESCRIPTION OF EMBODIMENTS

Figure 1:
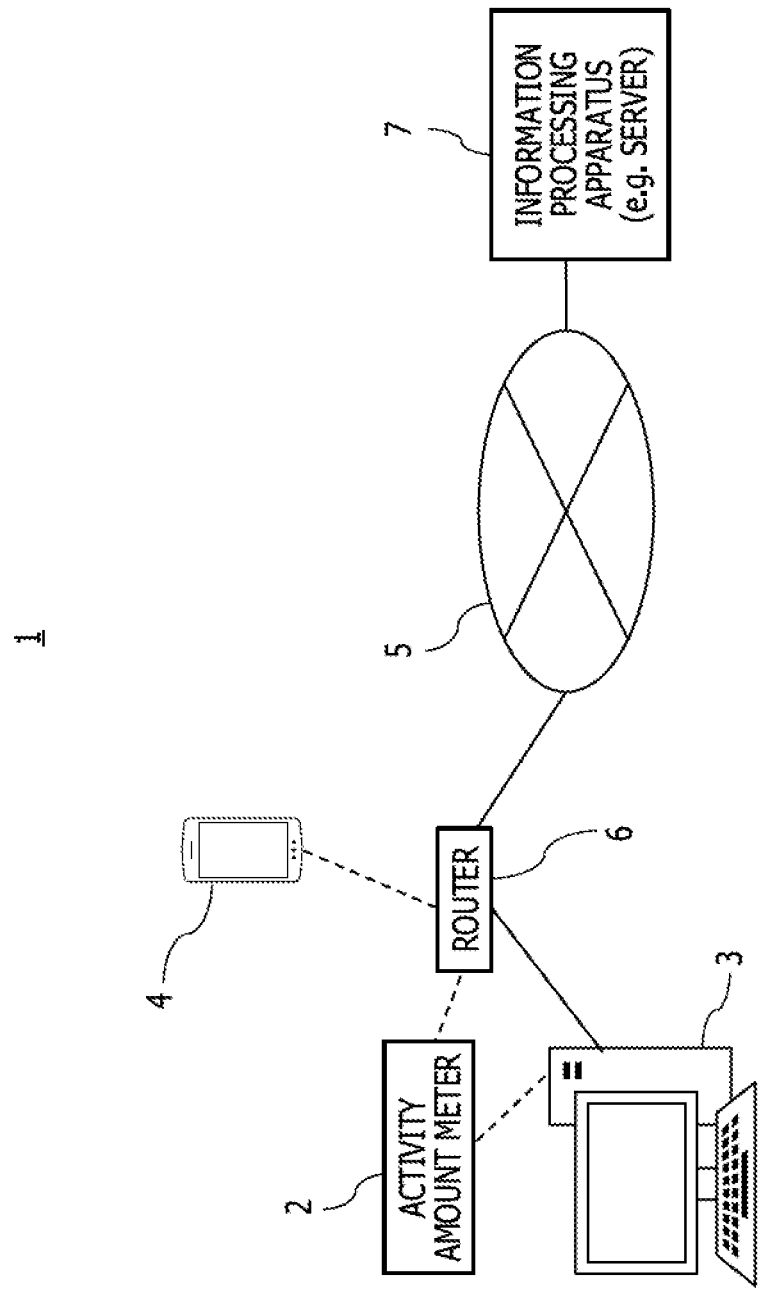
FIG. 1 is a block diagram illustrating a configuration example of an information processing system according to an embodiment.

However, it is requested to insert a measuring probe into the rectum of a test subject while measuring the rectal temperature, and it is requested to attach a measuring patch on the chest of a test subject while measuring the heartbeat. In addition, in order to estimate the biorhythm, the measurement for obtaining biological information is requested to be continuously carried out for 24 or more hours.

Accordingly, the test subject undergoes pain, discomfort, and the like due to the invasive measurement, and the long-time measurement continuously carried out for 24 or more hours interferes with everyday life of the test subject. As discussed above, it is difficult for the known biorhythm estimation technique to estimate or detect biorhythms of test subjects with ease.

The techniques to detect biorhythms with ease may be provided.

A biorhythm is a periodic rhythm that a biological body autonomously beats, and in a case of a person, physiological fluctuations of sleep, body temperature, blood pressure, autonomic nerves, and the like are adjusted taking about 24 hours as one cycle. The biorhythm of a person is also referred to as a "circadian rhythm".

The "circadian rhythm" is usually synchronized with a cycle (about 24 hours) of light and dark of morning and night. A case in which the "circadian rhythm" is disordered and is not synchronized with a cycle of about 24 hours (may also be referred to as "standard rhythm") is considered likely to affect the symptoms of jet lag, sleep trouble, seasonal depression, and the like. Therefore, treatment for improving the circadian rhythm is attracting attention.

The "circadian rhythm" of a test subject being shifted from the standard rhythm is considered likely to affect the exercise of physical performance of the test subject and the efficacy of medicines, and, for example, in the field of chronopharmacology, to maximize the efficacy or the like by normalizing the circadian rhythm is attracting attention. Accordingly, a technique capable of detecting the circadian rhythm of a test subject with ease is expected to be achieved.

For example, in a case where it is attempted to continuously measure the hair-root cells, blood, rectal temperature, or the like of a test subject for more than 24 hours in order to detect a circadian rhythm, the stated attempt will interfere with everyday life of the test subject. Accordingly, it may be difficult to apply the above-described measurement in everyday life.

In addition, the test subject sleeps with a hormone (for example, melatonin) having influence on sleep being secreted by the circadian rhythm, but it is difficult to directly know the secretion of the hormone by, for example, a blood test.

Therefore, in the present embodiment, an attempt is made to detect periodicity derived from a biorhythm of a test subject based on data indicating an amount of activity including an activity state and a sleeping state of everyday life of the test subject. The "amount of activity" of the test subject may be rephrased as an "amount of movement" of the test subject. Further, the data indicating the amount of activity of the test subject may be shortly referred to as "activity amount data".

In order to obtain, from the activity amount data, periodicity derived from the biorhythm, it is desirable that disturbance-induced factors (for example, movement following physical activities of the test subject) different from physiological fluctuations of the test subject be separated from the activity amount data.

If the above separation is allowed to be carried out, it is possible to find temporal "waves" of the amount of activity in a time period of about 24 hours, that is, the periodicity derived from the biorhythm.

Therefore, the inventor of the present application has found that it is possible to detect a biorhythm of a test subject with ease by detecting, for example, a component that represents one cycle with a time period of about 24 hours in a time waveform of activity amount data and that is unlikely to be affected by the movement following the physical activities of the test subject. Note that "time waveform of activity amount data" may, in short, be referred to as "time waveform of activity amount".

Hereinafter, embodiments will be described with reference to the drawings. However, the embodiments described below are merely examples and are not intended to exclude an application of various modifications or techniques which are not explicitly described below. Further, various exemplary aspects described below may be appropriately combined and carried out. Elements or components assigned the same reference numerals in the drawings used for the following embodiments will represent identical or similar elements or components unless otherwise specified.

FIG. 1 is a block diagram illustrating a configuration example of an information processing system according to an embodiment. An information processing system 1 illustrated in FIG. 1 may illustratively include an activity amount meter 2, a personal computer (PC) 3, a mobile terminal 4, a network 5, a router 6, and an information processing apparatus 7.

The activity amount meter 2 is also called "life coder 2", and illustratively measures data (may also be referred to as "activity amount data") indicating an amount of activity corresponding to the movement of a human body as an example of a biological body. The activity amount meter 2 may be a contact type or may be a non-contact type. A "person" as a measurement target for the activity amount meter 2 may also be called a "user", "observation target", or "test subject".

The number of test subjects may be plural, and an amount of activity of each of the plural test subjects may be measured by an individual activity amount meter 2. Alternatively, the activity amount meter 2 may be shared by some of or all of the plural test subjects. In a case where a single activity amount meter 2 is shared by the plural test subjects, the activity amount meter 2 may separately store the measurement results in a memory or the like for each of the plural test subjects.

Activity amount data obtained by the activity amount meter 2 may appropriately be inputted to the PC 3. The activity amount meter 2 may illustratively communicate with the PC 3 and input the activity amount data to the PC 3. The PC may be a desktop PC, a notebook PC (or laptop PC), a tablet PC, or the like.

The connection between the activity amount meter 2 and the PC 3 may be a wired connection or may be a wireless connection. Further, the communication between the activity amount meter 2 and the PC 3 may be communication through the router 6, or may be direct communication not through the router 6.

For the wired connection, as a non-limiting example, an applicable communication cable such as a local area network (LAN) cable or a Universal Serial Bus (USB) cable may be used. For the wireless connection, an applicable wireless communication system such as "Wireless Fidelity (WiFi)" (registered trademark), "Bluetooth" (registered trademark), or Near Field Communication (NFC) may be used.

The PC 3 may be communicably coupled to the router 6, and may be capable of communicating with the information processing apparatus 7 via the network 5. Note that the "PC" is also an example of an "information processing apparatus".

The connection between the PC 3 and the router 6 may be a wired connection or may be a wireless connection. For the wired connection, as a non-limiting example, an applicable communication cable such as a LAN cable or a USB cable may be used. For the wireless connection, as a non-limiting example, an applicable wireless communication system such as "WiFi" or "Bluetooth" may be used.

The network 5 may illustratively be the Internet, a LAN, a wide area network (WAN), or the like. Further, the network 5 may include a wireless access network. The wireless access network may illustratively be a wireless access network based on the Long Term Evolution (LTE), the LTE-Advanced, or the like of the 3rd Generation Partnership Project (3GPP).

The information processing apparatus 7 may be a PC, or may be a server computer (may also be referred to as "server"). The server may be a cloud server installed in a data center or the like. Hereinafter, for the sake of convenience, it is assumed that the information processing apparatus 7 is a "server". The server 7 may receive and acquire the activity amount data by communicating with the PC 3 via the network 5.

In a case where the activity amount meter 2 is communicably coupled to the router 6 being coupled with the network 5, the server 7 may receive and acquire the activity amount data from the activity amount meter 2 via the network 5, not through the PC 3.

The connection between the activity amount meter 2 and the router 6 may be a wired connection or may be a wireless connection. For the wired connection, an applicable communication cable such as a LAN cable or a USB cable may be used. For the wireless connection, an applicable wireless communication system such as "WiFi", "Bluetooth", or "NFC" may be used.

Alternatively, the server 7 may receive and acquire, not through the router 6 but through the wireless access network, the activity amount data obtained by the activity amount meter 2.

The activity amount data may be measured by the mobile terminal 4. For example, the mobile terminal 4 may be provided with a function equivalent to part of or all of the function of the activity amount meter 2. The mobile terminal 4 may be a cellular phone such as a smartphone, or may be a wearable terminal.

The activity amount data obtained by the mobile terminal 4 may be received and acquired by the PC 3, the server 7, or the like through a communication path similar to that for the activity amount data obtained by the activity amount meter 2.

The activity amount data supplied from the activity amount meter 2, the mobile terminal 4, or the like to the PC 3, the server 7, or the like may be such data that all or part of the data has been processed or manipulated in the activity amount meter 2, the mobile terminal 4, or the like.

The PC 3, the server 7, or the like having acquired the activity amount data processes the acquired activity amount data. The processing of the activity amount data may include memorizing and managing the activity amount data. The managing of the activity amount data may include compiling the activity amount data in a database (DB). The data compiled in the DB may be referred to as "cloud data", "big data", or the like.

The PC 3, the server 7, or the like may detect a biorhythm of the test subject based on the acquired activity amount data. The "detection" of the biorhythm may also be referred to as "measurement", "determination", or "estimation".

Accordingly, the PC 3, the server 7, or the like may also be referred to as a device for biorhythm detection, a device for biorhythm measurement, a device for biorhythm determination, or a device for biorhythm estimation. Hereinafter, for the sake of convenience, the PC 3, the server 7, or the like is referred to as a "biorhythm detection device" in some cases.

The function, processing (or algorithm), and the like as the biorhythm detection device may be realized by a single PC or server, or may be realized by distributed processing by a plurality of PCs, servers, and the like.

In other words, detection processing for the activity amount data, the biorhythm based on the activity amount data, or the like may be processed or managed by a single information processing apparatus, or may be processed or managed by a plurality of information processing apparatuses in a distributed manner.

(Configuration Example of Activity Amount Meter 2)

Figure 2:
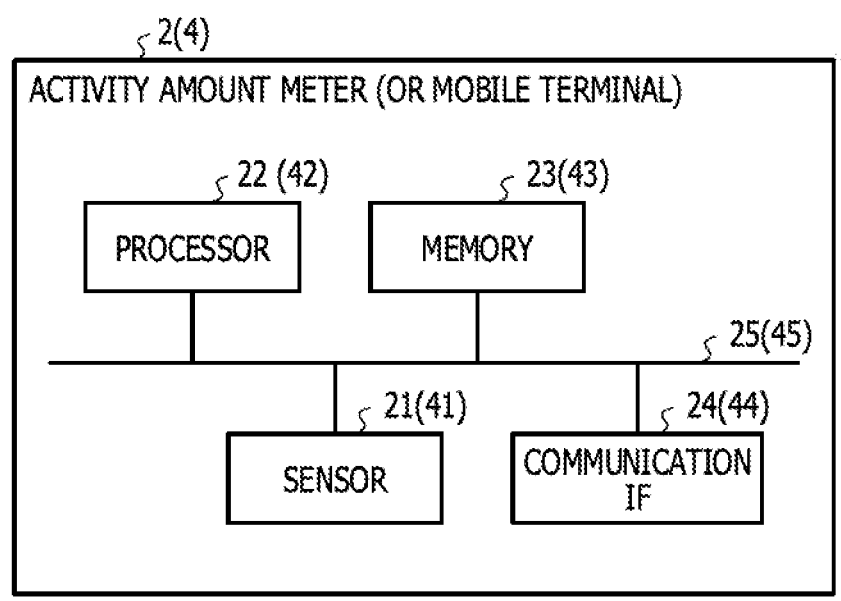
FIG. 2 is a block diagram illustrating a configuration example of an activity amount meter (or a mobile terminal) exemplified in FIG. 1.

FIG. 2 illustrates a configuration example of the activity amount meter 2. Also, the mobile terminal 4 capable of measuring the activity amount data may have a configuration exemplified in FIG. 2, and elements of the mobile terminal 4 are indicated by reference numerals in parentheses.

Hereinafter, in order to avoid redundant description, elements 21 to 25 of the activity amount meter 2 will be described. In FIG. 2, the elements of the mobile terminal 4 indicated by reference numerals 41 to 45 in parentheses may be considered to have equivalent functions to those of the elements 21 to 25 of the activity amount meter 2 unless otherwise specified.

As illustrated in FIG. 2, the activity amount meter 2 may illustratively include an activity amount sensor 21, a processor 22, a memory 23, and a communication interface (IF) 24. The activity amount sensor 21, the processor 22, the memory 23, and the communication IF 24 may illustratively be coupled to a bus 25, and may be capable of communicating with each other through the processor 22.

It is sufficient that the activity amount sensor 21 (hereinafter, referred to as "sensor 21" in some cases) is illustratively a sensor which is capable of sensing the activity amount data corresponding to the activity of a biological body. Note that the activity amount data is an example of vital information. The activity amount data sensed by the sensor 21 may be referred to as "sensor data" for the sake of convenience. The term of "sensing" may be referred to as "detection" or "measurement".

As a non-limiting example, an inertial sensor, a radio wave sensor, a heartbeat sensor, a pulse sensor, or the like may be applied to the sensor 21 capable of measuring the activity amount data of a biological body.

The inertial sensor may be an acceleration sensor or a gyroscope. Any one of piezoelectric type and capacitive type sensors may be illustratively applied to the acceleration sensor. Any one of a rotary machine (flywheel) type, an optical type, and a vibrating structure type sensor may be applied to the gyroscope.

The inertial sensor may include one or more detection axes. A gravity component in a direction along the detection axis may be detected as "acceleration", for example. The detection of "acceleration" makes it possible to detect activity amount data in response to movement, posture, or the like of the biological body.

It is possible for the radio wave sensor to detect the movement of the biological body in a non-contact manner in which the radio wave sensor radiates radio waves such as microwaves to a sensing target, receives reflective waves, which are reflected at the sensing target, and detects the movement of the target based on a change of the reflective waves.

For example, in a case where a distance between the radio wave sensor and the sensing target is changed, a change occurs in the reflective waves due to the Doppler effect. The change of the reflective waves may be illustratively acquired as a change in one or both of amplitude and a frequency of the reflective waves. The "radio wave sensor" may be referred to as a "microwave sensor", a "radio frequency (RF) sensor", or a "Doppler sensor".

The heartbeat sensor illustratively detects the pulse-beat of a blood vessel in response to the heartbeat of the biological body. For example, the heartbeat of the biological body may be acquired as a change of electromagnetic waves, pressure, or sound in response to the beating of the heart.

Illustratively, when a blood vessel of a finger, an earlobe or the like is irradiated with light such as infrared rays, the reflective light changes periodically in accordance with a rhythmical change of the bloodstream and the light absorption characteristics. Hence, it is possible to optically measure the heartbeat as a fluctuation of the reflective light in accordance with the bloodstream change.

Alternatively, when a biological body is irradiated with radio waves such as microwaves, a rhythmical motion occurs in a surface (for example, skin) of the biological body in accordance with beating of the heart, whereby a distance between the skin and a radio wave transmission source changes in accordance with the motion, and thus a change occurs in the reflective waves due to the Doppler effect.

Hence, it is also possible to measure the heartbeat of the biological body as a fluctuation in reflection, due to the Doppler effect, of the waves radiated on the biological body. To rephrase, the radio wave sensor may be used for the heartbeat sensor.

Further, when the heart is contracted and relaxed rhythmically, the pressure of a blood vessel (hereinafter, may be referred to as "blood pressure") is also fluctuated, whereby it is also possible to measure the heartbeat as a rhythmical fluctuation of the blood pressure by using a pressure sensor, a piezoelectric sensor, or the like.

Furthermore, it is also possible to measure the heartbeat as a change of electric potential of the heart muscle or a change of sound corresponding to the heart beating like in a case of using an electrocardiograph or a phonocardiograph.

As described above, since the information indicative of the heartbeat may be considered as being equivalent to the information indicative of the pulse in some cases, the "heartbeat sensor" may be referred to as a "pulse sensor".

The activity amount meter 2 including the sensor 21 may also be referred to as "sensor unit 2" for the sake of convenience. The sensor unit 2 may illustratively be mounted in contact with the skin of a human body, or mounted at a position separate from the human body in a non-contact state within a range where it is possible to sense the vital information.

The activity amount data supplied from the activity amount meter 2, the mobile terminal 4, or the like to the PC 3, the server 7, or the like may be primary data detected by the sensor 21 or may be secondary data obtained based on the detected data. To rephrase, it is sufficient for the activity amount data to be such data that represents the movement corresponding to the activity of everyday life of the test subject.

The processor 22 is an example of an arithmetic processing unit having the capability of arithmetic processing. The arithmetic processing unit may be referred to as an arithmetic processing device or an arithmetic processing circuit. A central processing unit (CPU), a digital signal processor (DSP), a micro processing unit (MPU), an integrated circuit (IC), or the like may be illustratively applied to the arithmetic processing unit. The "processor" may be referred to as a "processing unit", a "controller" or a "computer".

The processor 22 illustratively implements a function, processing, and the like as the activity amount meter 2, and controls operations corresponding to the function, processing, and the like. A program, data, and the like to implement the function, processing, control, and the like as the activity amount meter 2, may be stored in the memory 23.

The "program" may be referred to as "software" or an "application". The "data" may include the activity amount data and the data generated according to the operations of the processor 22.

The processor 22 is configured to operate while reading the program, data, and the like stored in the memory 23, by which the function, processing, and control as the activity amount meter 2 are implemented. The memory 23 is an example of a storage medium, and may be a random access memory (RAM), a flash memory, or the like.

All or part of program codes configuring a program may be stored in a storage section or may be described as part of an operating system (OS).

Programs and data may be recorded in a computer-readable recording medium to be provided. As examples of recording media, flexible disks, CD-ROMs, CD-Rs, CD-RWs, MOs, DVDs, Blu-ray disks, portable hard disks, and the like may be cited. Further, a semiconductor memory such as a Universal Serial Bus (USB) memory is also an example of the recording media.

Alternatively, programs and data may be provided (for example, downloaded) from the server or the like to the activity amount meter 2 via the network 5. For example, the programs and the data may be provided to the activity amount meter 2 through the communication IF 24.

The communication IF 24 is an example of a communication unit included in the activity amount meter 2, and illustratively makes it possible to communicate with the PC 3, the router 6, and the wireless access network. The activity amount data obtained by the sensor 21 or the processor 22 may be transmitted to the PC 3, the server 7, and the like through the communication IF 24.

(Configuration Example of the PC 3)

Figure 3:
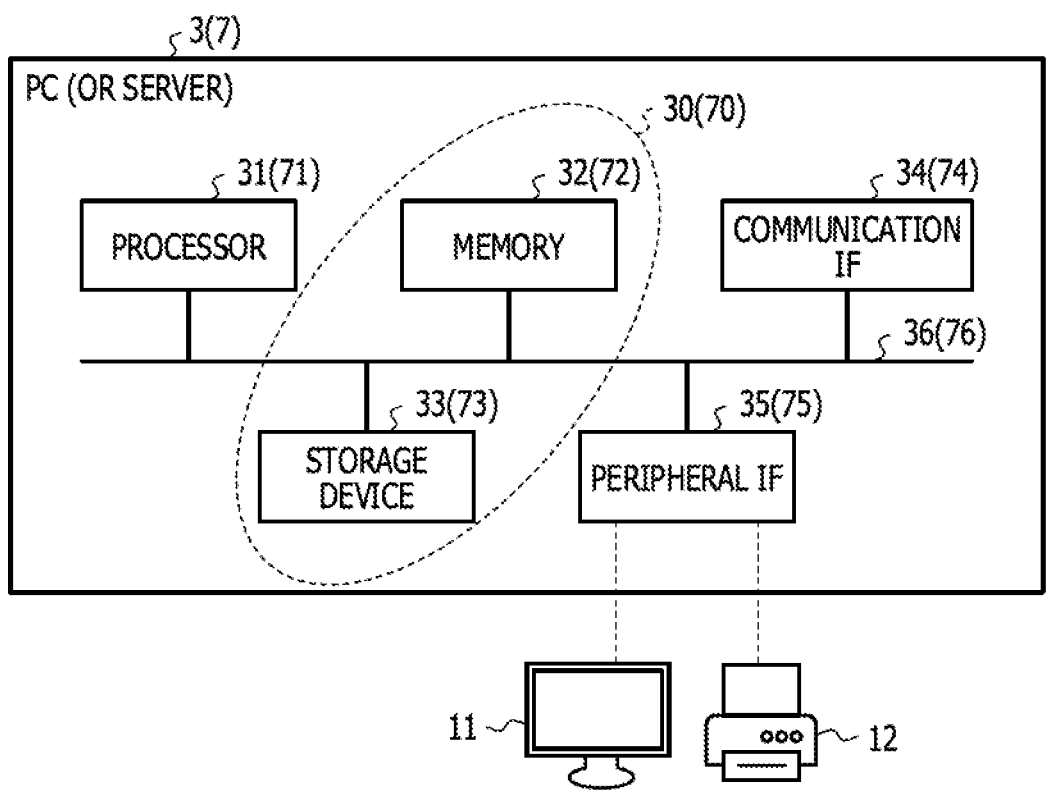
FIG. 3 is a block diagram illustrating a configuration example of a personal computer (PC) (or a server) exemplified in FIG. 1.

Next, FIG. 3 illustrates a configuration example of the PC 3. Since the PC 3 is an example of an information processing apparatus, the configuration thereof may be similar to that of the server 7. Therefore, elements of the server 7 are indicated by reference numerals 71 to 76 in parentheses in FIG. 3.

Hereinafter, in order to avoid a redundant description, elements 31 to 36 of the PC 3 will be described. In FIG. 3, the elements of the server 7 indicated by the reference numerals 71 to 76 in parentheses may be considered to have equivalent functions to those of the elements 31 to 36 of the PC 3 unless otherwise specified.

As illustrated in FIG. 3, the PC 3 may illustratively include a processor 31, a memory 32, a storage unit 33, a communication IF 34, and a peripheral IF 35. The processor 31, the memory 32, the storage unit 33, the communication IF 34, and the peripheral IF 35 may be illustratively coupled to a bus 36, and may be capable of communicating with each other through the processor 31.

The processor 31 is an example of an arithmetic processing unit having the capability of arithmetic processing. The arithmetic processing unit may be referred to as an arithmetic processing device or an arithmetic processing circuit. A central processing unit (CPU), a digital signal processor (DSP), a micro processing unit (MPU), an integrated circuit (IC), or the like may be illustratively applied to the arithmetic processing unit. The "processor" may be referred to as a "processing unit", a "controller", or a "computer".

The processor 31 illustratively causes the PC 3 to function or perform processing as a biorhythm detection device, and controls the operations corresponding to the function and the processing. A program and data to implement the function, processing, and control as the biorhythm detection device 3, may be stored in the memory 32 and the storage unit 33.

The processor 31 is configured to operate while reading the program and the data stored in the memory 32 and the storage unit 33, by which the function, processing, and control as the biorhythm detection device 3 are implemented.

The memory 32 is an example of a storage medium, and may be a RAM, a flash memory, or the like.

The storage unit 33 may store various types of data and programs. A hard disk drive (HDD), a solid state drive (SSD), a flash memory, or the like may be used for the storage unit 33.

The data stored in the storage unit 33 may illustratively include the activity amount data received through the communication IF 34. The data stored in the storage unit 33 may be appropriately compiled in a database (DB). The data compiled in the DB may be referred to as "cloud data", "big data", or the like.

The storage unit 33 and the memory 32 may be collectively referred to as a "storage section 30" of the PC 3. Likewise, the storage unit 33 and the memory 32 in the server 7 may also be collectively referred to as a "storage section 70".

The programs stored in the storage section 30 may include a program to carry out processing, which will be described later with reference to FIGS. 4, 21, and 22. The program may be referred to as a "biorhythm detection program" for the sake of convenience.

All or part of program codes configuring a program may be stored in the storage section or may be described as part of an OS.

Programs and data may be recorded in a computer-readable recording medium to be provided. As examples of recording media, flexible disks, CD-ROMs, CD-Rs, CD-RWs, MOs, DVDs, Blu-ray disks, portable hard disks, and the like may be cited. Further, a semiconductor memory such as a Universal Serial Bus (USB) memory is also an example of the recording media.

Alternatively, programs and data may be provided (for example, downloaded) from the server or the like to the activity amount meter 2 via the network 5. For example, the programs and the data may be provided to the PC 3 through the communication IF 34.

The communication IF 34 is an example of a communication unit included in the PC 3, and illustratively makes it possible to communicate with the activity amount meter 2, the mobile terminal 4, the router 6, the wireless access network, and the like.

Focusing on reception processing, the communication IF 34 is an example of a receiver (which may be referred to as an "acquisition unit") configured to receive the activity amount data obtained by the activity amount meter 2 and the mobile terminal 4. On the other hand, focusing on transmission processing, the communication IF 34 is an example of a transmitter configured to transmit the activity amount data obtained by the activity amount meter 2 and the mobile terminal 4 to the server 7, for example.

A communication IF 74 of the server 7 is illustratively capable of transmitting data to the activity amount meter 2, the PC 3, and the mobile terminal 4 via the network 5. The data transmitted to the activity amount meter 2, the PC 3, and the mobile terminal 4 may illustratively include a processed result of the activity amount data (for example, a determination result of a circadian rhythm).

The peripheral IF 35 is illustratively an interface for coupling peripheral devices to the PC 3. The peripheral devices may include input devices configured to input information to the PC 3, and output devices configured to output the information generated by the PC 3.

The input devices may include a keyboard, a mouse, a touch panel, and the like. The output devices may include a display 11, a printer 12, and the like, as schematically exemplified in FIG. 3.

Operation Example

Hereinafter, an operation example of the above-discussed information processing system 1 will be described with reference to FIGS. 4 to 20. Note that in the following description of the operation example, for the sake of convenience, an example in which the PC 3 operates as a "biorhythm detection device" and carries out a detection process of a circadian rhythm based on activity amount data will be described. Further, it is assumed that the activity amount data processed by the biorhythm detection device 3 is activity amount data measured by the activity amount meter 2.

Note that, all or part of the operation example described below may apply to an operation example of the server 7 (for example, a processor 71), which operates as a "biorhythm detection device". Further, in the operation example described below, "the activity amount meter 2" may be replaced with "the mobile terminal 4".

Figure 4:
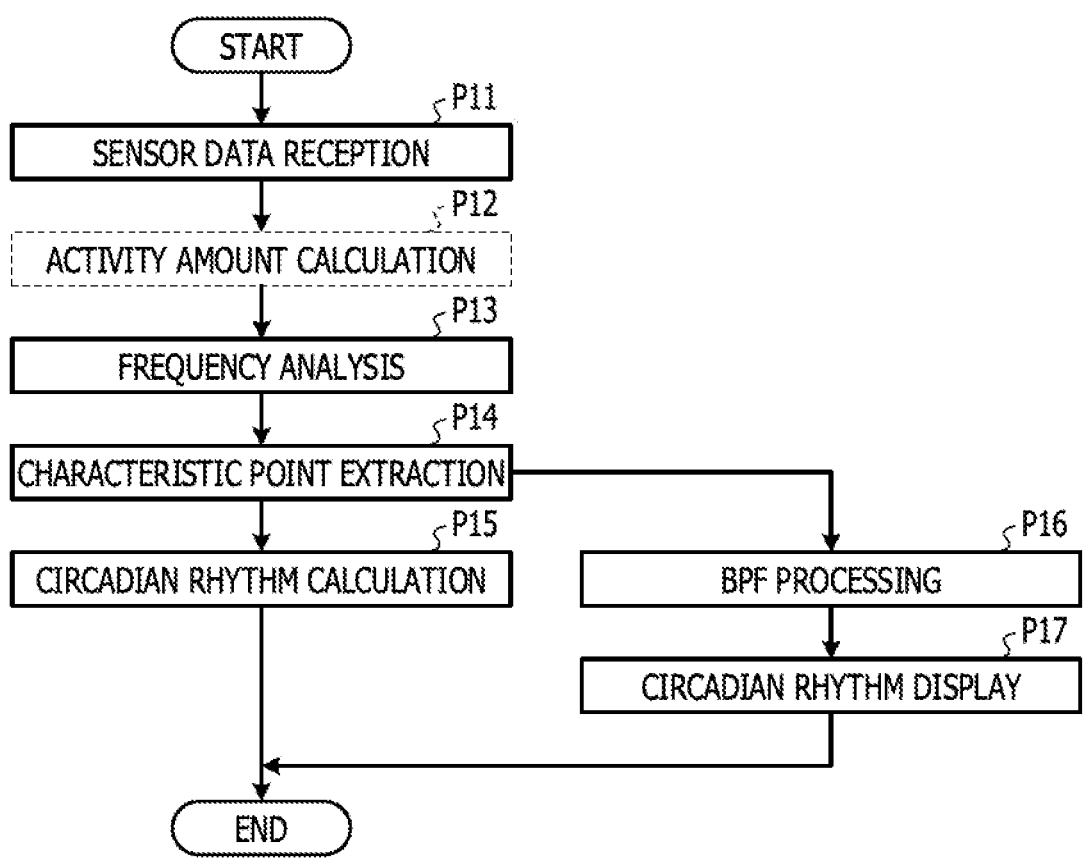
FIG. 4 is a flowchart for describing an operation example of an information processing system (a biorhythm detection device) according to an embodiment.

FIG. 4 is a flowchart illustrating an operation example of the biorhythm detection device 3. The flowchart exemplified in FIG. 4 may be illustratively executed by the processor 31 of the biorhythm detection device 3.

As exemplified in FIG. 4, the biorhythm detection device 3 receives sensor data measured by the activity amount meter 2 (processing P11).

The sensor data may be activity amount data, or may be data from which it is possible to calculate activity amount data. In the case of the latter one from which it is possible to calculate the activity amount data, the biorhythm detection device 3 may calculate the activity amount data based on the data from which it is possible to calculate the activity amount data (processing P12).

Figure 5:
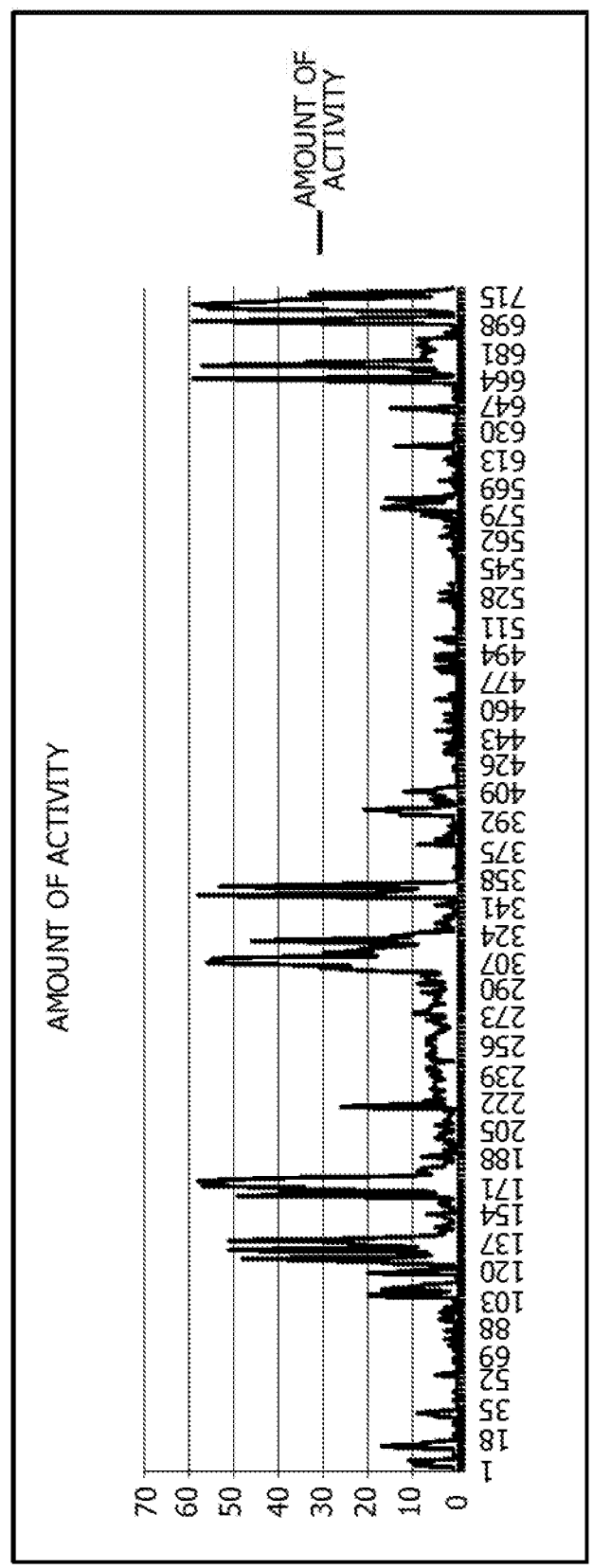
FIG. 5 is a graph illustrating an example of activity amount data measured by an activity amount meter.

FIG. 5 illustrates an example of the activity amount data. In FIG. 5, as a non-limiting example, a change in activity amount of a test subject for one day (=24 hours) is illustrated in the case of using an inertial sensor as the activity amount sensor 21 (or 41).

In FIG. 5, the horizontal axis represents time (illustratively represents sampling times), and the vertical axis represents activity amount power. The horizontal axis of FIG. 5 indicates that, as a non-limiting example, activity amount data is sampled 720 times in 24 hours and 720 pieces of sampling data (may be referred to as "time series data") are obtained. To rephrase, the sampling rate of the activity amount data is 720 Hz.

Figure 6:
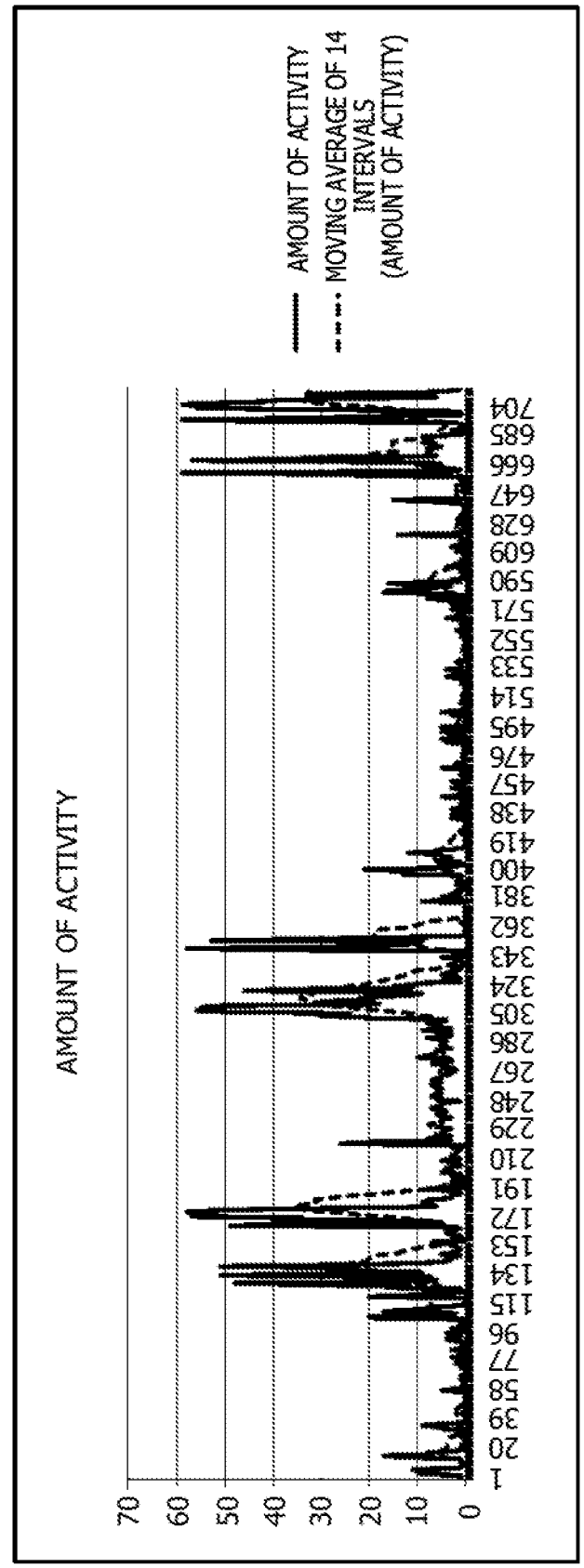
FIG. 6 is a graph illustrating an example in which calculated is a moving average with respect to the activity amount data exemplified in FIG. 5.
Figure 7:
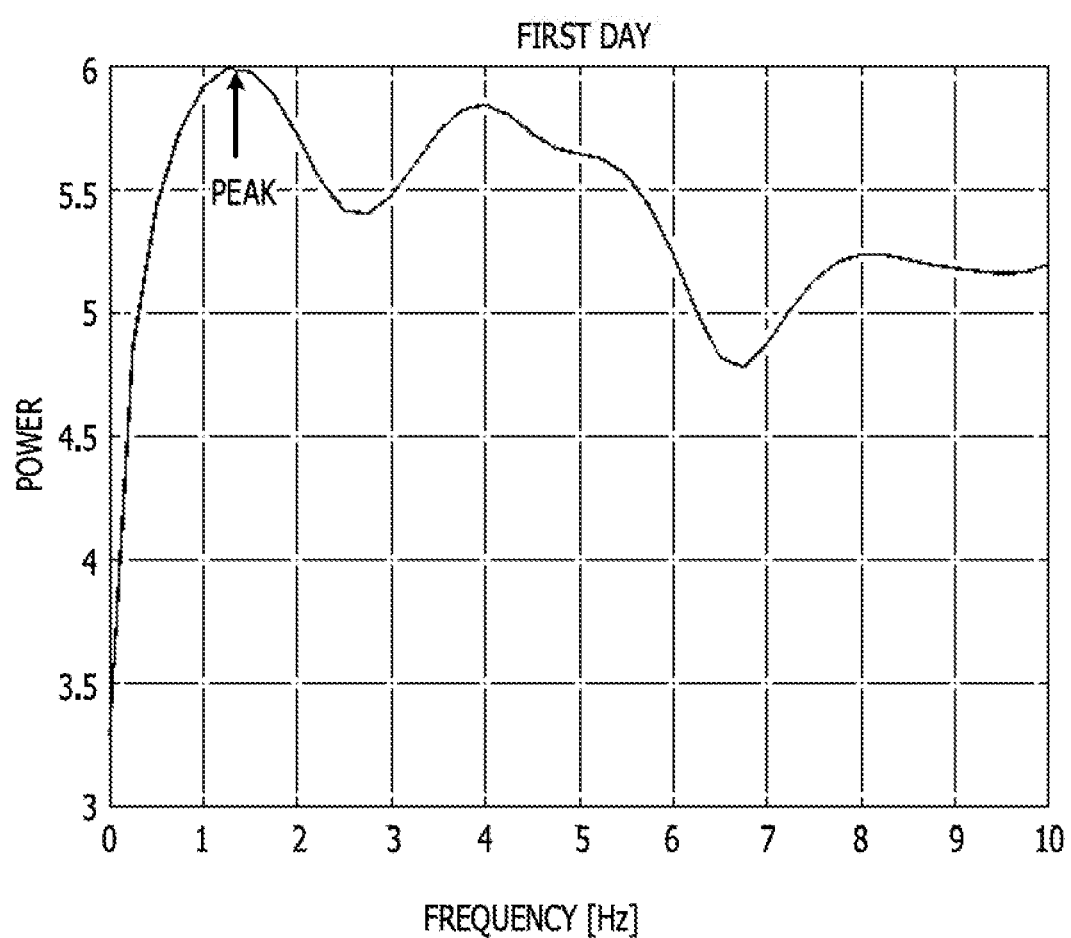
FIG. 7 is a graph illustrating an example of a result of frequency analysis performed on activity amount data of the first day of a week (seven days).
Figure 8:
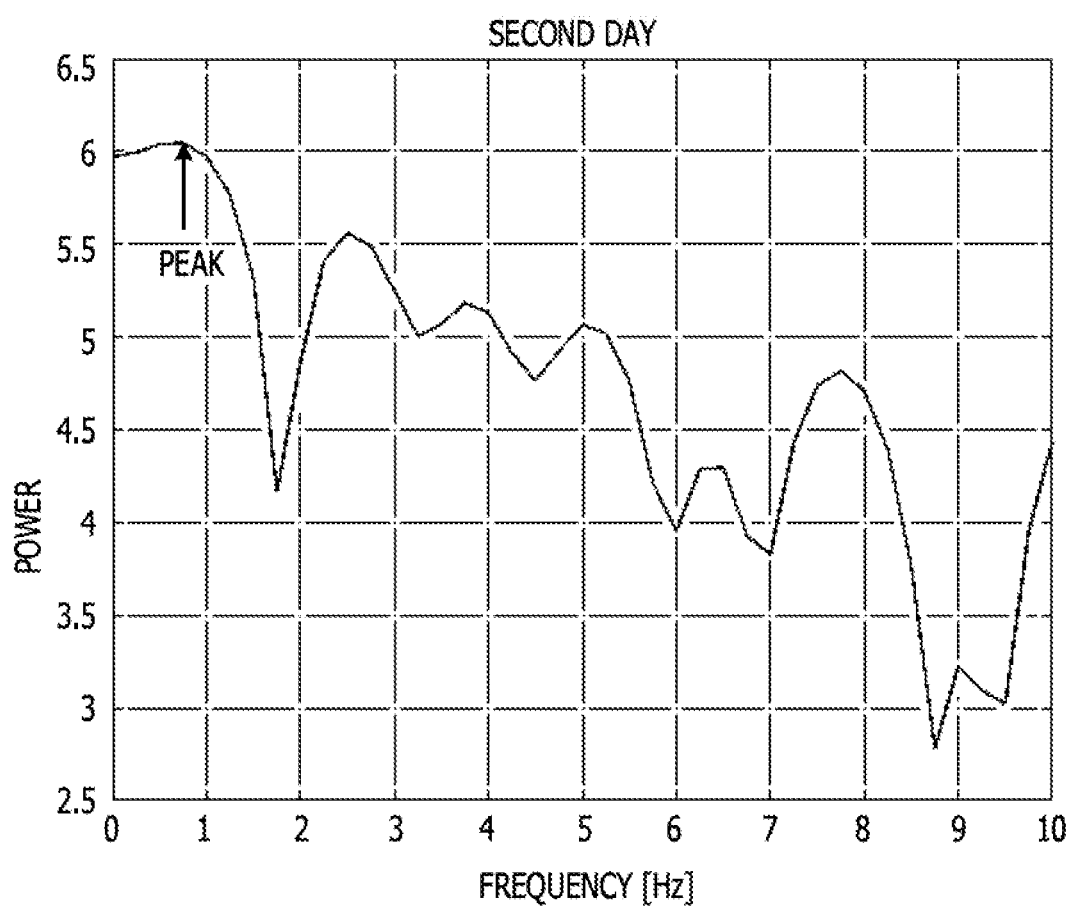
FIG. 8 is a graph illustrating an example of a result of frequency analysis performed on activity amount data of the second day of a week (seven days).
Figure 9:
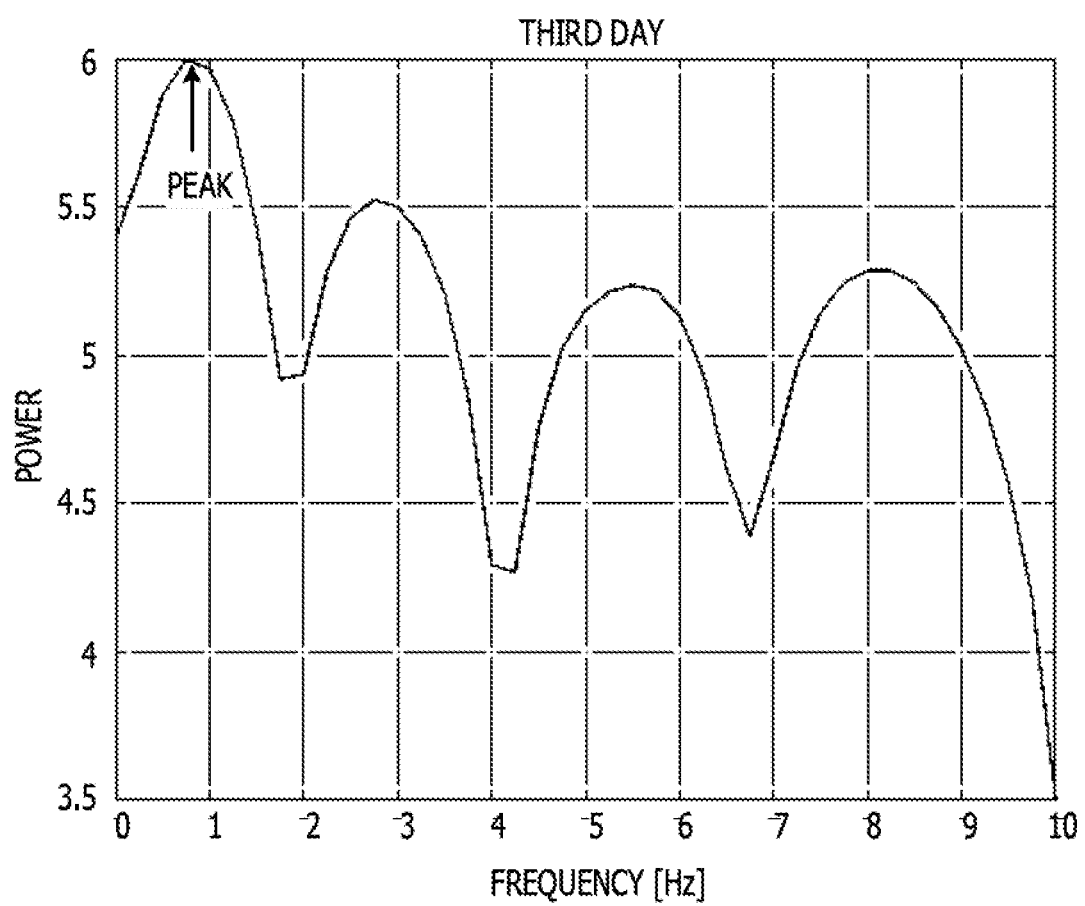
FIG. 9 is a graph illustrating an example of a result of frequency analysis performed on activity amount data of the third day of a week (seven days).
Figure 10:
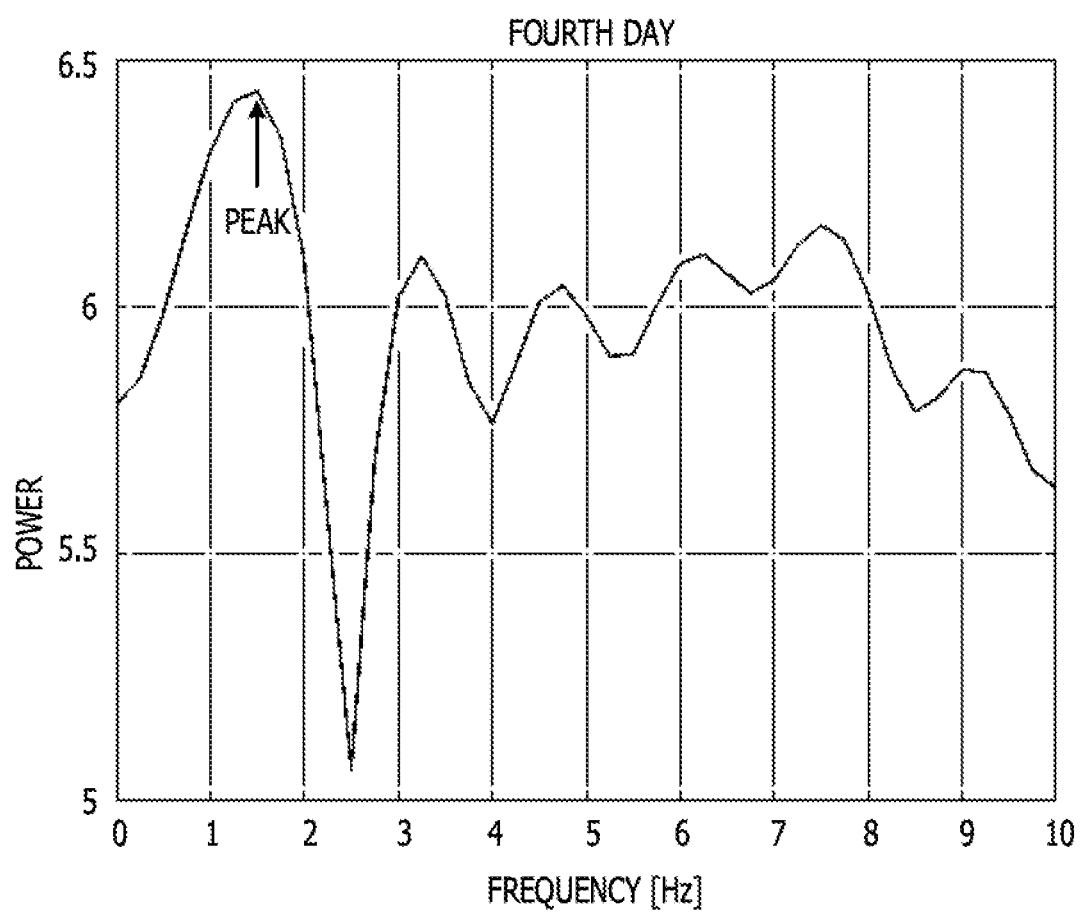
FIG. 10 is a graph illustrating an example of a result of frequency analysis performed on activity amount data of the fourth day of a week (seven days).
Figure 11:
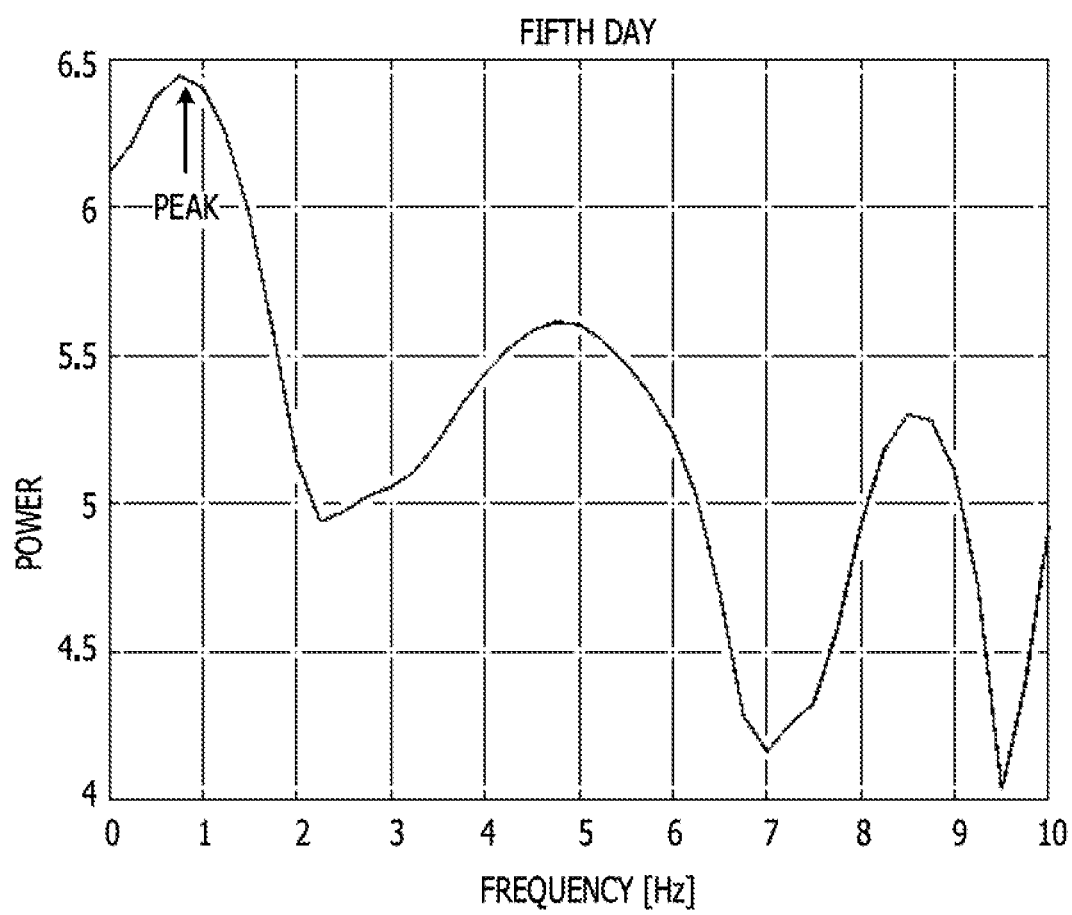
FIG. 11 is a graph illustrating an example of a result of frequency analysis performed on activity amount data of the fifth day of a week (seven days).
Figure 12:
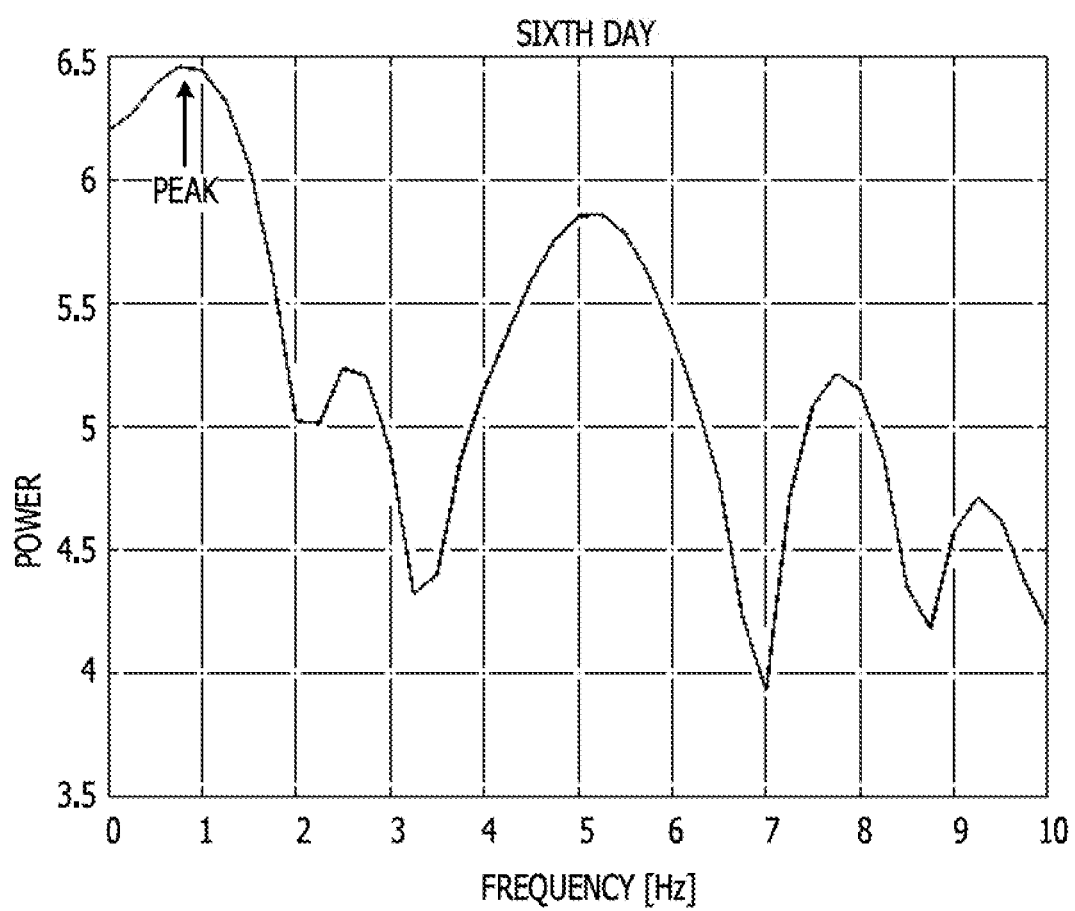
FIG. 12 is a graph illustrating an example of a result of frequency analysis performed on activity amount data of the sixth day of a week (seven days).
Figure 13:
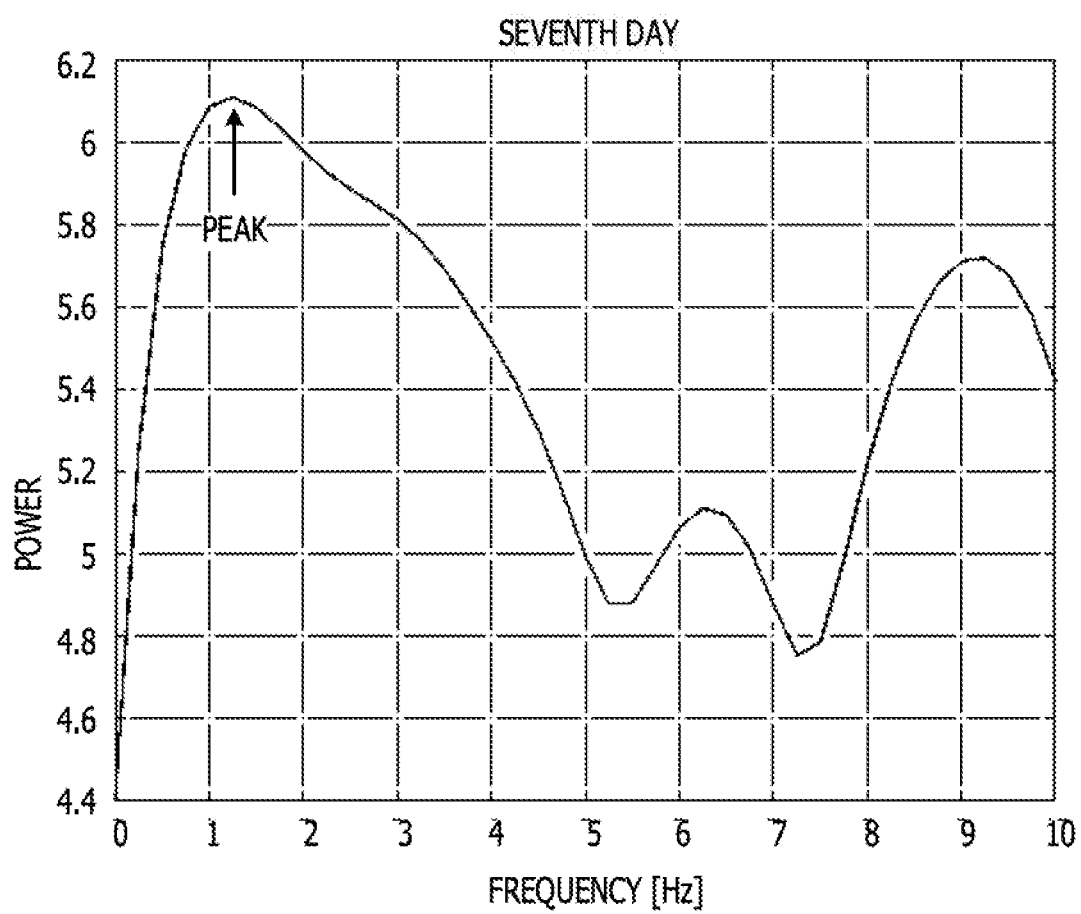
FIG. 13 is a graph illustrating an example of a result of frequency analysis performed on activity amount data of the seventh day of a week (seven days).

The biorhythm detection device 3 detects, from the activity amount data as exemplified in FIG. 5, a circadian rhythm of the test subject (in other words, periodicity of approximately 24 to 25 hours). Here, in a case where the activity amount data of 24 hours is smoothed by calculating a moving average of, for example, 14 intervals with respect to the time series activity amount data exemplified in FIG. 5, a certain periodicity appears as illustrated in FIG. 6, for example.

However, since the periodicity depends on the magnitude of the original activity amount data (may be referred to as "raw data"), in other words, depends on the magnitude of the movement following the activity of the test subject, the stated periodicity is largely different from the period of the circadian rhythm. Therefore, it is difficult to detect a circadian rhythm even if the activity amount data is smoothed by the moving average.

Then, the biorhythm detection device 3 (for example, the processor 31) according to the present embodiment illustratively acquires the time-series activity amount data as a time waveform and performs frequency analysis on the time waveform (processing P13), and detects and extracts a characteristic point in the frequency analysis result (processing P14).

The fast Fourier transform (FFT) or the discrete Fourier transform (DFT) may be applied to the frequency analysis. The "characteristic point" is a characteristic frequency indicating the periodicity of the circadian rhythm. For example, the "characteristic point" may be a frequency component having a peak of power spectrum density (which may be referred to as "peak power") in the frequency analysis result.

In FIGS. 7 to 13, examples of the results of frequency analysis performed on the activity amount data of one week (seven days) are illustrated. In each of FIGS. 7 to 13, the horizontal axis represents a frequency, and the vertical axis represents power. The biorhythm detection device 3 may search for a frequency having peak power (see arrow mark) and may detect and extract the stated frequency as a "characteristic point", in each of the frequency analysis results exemplified in FIGS. 7 to 13.

As exemplified in FIGS. 7 to 13, the frequency having peak power (which may be referred to as "peak frequency" for the sake of convenience) is a frequency which completes one cycle near approximately 24 hours a day. In the case where 24 hours a day are illustratively defined as 1 Hz in a pseudo manner, the biorhythm detection device 3 may search for a peak frequency closest to 1 Hz in the frequency analysis result.

The reason why 24 hours a day are defined as 1 Hz in the pseudo manner is as follows. For example, in a case where a period is represented as T[sec], a frequency f[Hz] of the wave is represented by an equation of f=1/T[Hz]. Since 24 hours are equal to a value of 60 sec.×60×24=86400 seconds, f becomes equal to 11.57[pHz] in a case where 24 hours a day correspond to one wavelength.

Here, in the case where the frequency analysis is performed on the activity amount data, 86400 samples are obtained by the activity amount data of 24 hours being sampled every second; in other words, in the case where the sampling rate is 86400 Hz, the frequency to be determined is not balanced with respect to the number of samples. Due to this, the amount of calculation becomes large compared to the number of samples.

Then, a single day is assumed to include just one second in a pseudo manner, and it is defined that a one-day period is equivalent to 1 Hz. The biorhythm detection device 3 finds a period of the peak frequency closest to 1 Hz in the frequency analysis result, so as to calculate a circadian rhythm as a biological rhythm (which may be referred to as "cycle") of one day of the test subject (processing P15 in FIG. 4).

The same result is obtained in a case of 86400 seconds being thinned out to be 1/120 thereof, that is, 720 seconds, or in a case of being accumulated. Therefore, it is possible to significantly reduce the amount of calculation by carrying out the processing in which the number of samples is decreased from 86400 to 720, that is, the sampling rate is set to be 720 Hz.

Since a single day is defined as 1 Hz in a pseudo manner, a frequency lower than 1 Hz may be set as a search frequency in the result obtained through the frequency analysis of the activity amount data of a time period such as 18 hours (¾ day) or 12 hours (½ day) that is shorter than 24 hours.

For example, in the case of the frequency analysis result of the ¾-day activity amount data, it is sufficient to search for a peak frequency closest to 0.75 Hz; in the case of the frequency analysis result of the ½-day activity amount data, it is sufficient to search for a peak frequency closest to 0.5 Hz.

To rephrase, the activity amount data or the frequency analysis result usable for detecting a circadian rhythm may be data of a time period less than 24 hours.

For example, since the circadian rhythm of a test subject may be reset by the test subject being exposed to sunlight, activity amount data of several hours from when the test subject wakes up in the morning may not exhibit a characteristic periodicity of the circadian rhythm.

Accordingly, in a case where 24 hours a day are divided by, for example, six hours into 4 parts, activity amount data or a frequency analysis result corresponding to the activity amount data or the frequency analysis result of about six to twelve hours (¼ day to ½ day) from the wakeup, may be excluded from candidates to be used in the calculation of a circadian rhythm. This makes it possible to reduce an amount of calculation processing for the circadian rhythm and suppress a decrease in calculation accuracy of the circadian rhythm.

FIG. 14 illustrates an example of a biorhythm (frequency f) of a test subject for each day obtained from the activity amount data of seven days exemplified in FIGS. 7 to 13.

It is possible for a rhythm Cir for one hour unit with respect to the frequency f ("calculated time" in FIG. 14) to be expressed by an equation of Cir=24/f. Thus, it is possible to obtain a time difference of the rhythm Cir with respect to 24 hours a day by "24−Cir".

Accordingly, from the data exemplified in FIG. 14, it is possible to detect and determine the degree of shift of the biorhythm of the individual test subject from 24 hours a day.

For example, in FIG. 14, since the frequency f of each of the first day, fourth day, and seventh day is higher than 1 Hz, the time difference of the rhythm with respect to 24 hours takes a "negative" value.

Accordingly, it is possible to determine that the circadian rhythm of the test subject is shorter (reduced) than 24 hours to be the standard time. The circadian rhythm being shorter than 24 hours may cause early-morning awakening, for example.

On the other hand, in FIG. 14, since the frequency f of each of the second day, third day, fifth day, and sixth day is lower than 1 Hz, the time difference of the rhythm with respect to 24 hours takes a "positive" value.

Accordingly, it is possible to determine that the circadian rhythm of the test subject is longer (extended) than 24 hours to be the standard time. The circadian rhythm being longer than 24 hours may bring about, for example, a symptom such as having difficulty in waking up or having difficulty in falling asleep at night.

Figure 15:
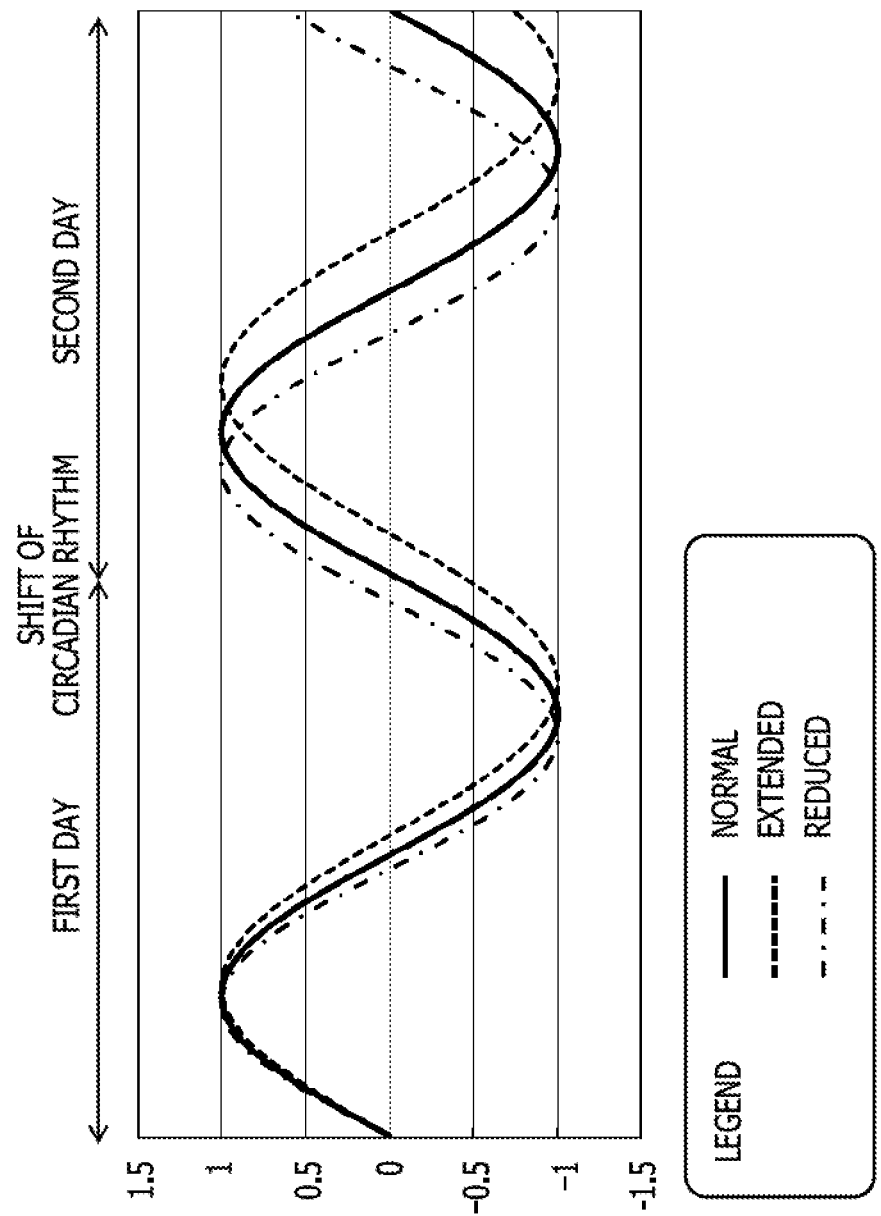
FIG. 15 is a graph illustrating time waveforms of biorhythms of a test subject along with a time waveform of a circadian rhythm to be a standard.

FIG. 15 illustrates an example of time waveforms of a rhythm Cir of two days of a test subject. In FIG. 15, a waveform depicted with a solid line represents a normal waveform in which the circadian rhythm of the test subject is close to 24 hours. In contrast, a waveform depicted with a dot-dash line represents a waveform of a case in which the circadian rhythm of the test subject is shorter than 24 hours, and a waveform depicted with a dotted line represents a waveform of a case in which the circadian rhythm of the test subject is longer than 24 hours.

The circadian rhythm beats a rhythm at a period of about 24 to 25 hours a day, and forms two wavelengths in two days in the case where the circadian rhythm is normal. In the case where the circadian rhythm becomes longer, since the circadian rhythm is less than two wavelengths, a body rhythm becomes slow so that a symptom such as having difficulty in waking up or having difficulty in falling asleep at night may be caused as discussed above. Conversely, in the case where the circadian rhythm becomes shorter, since the circadian rhythm exceeds two wavelengths in two days, the body rhythm becomes faster so that early-morning awakening may be caused as discussed above.

All the data regarding the items of "day", "frequency", "calculated time", and "time difference with respect to 24 hours" exemplified in FIG. 14 may be outputted to external devices (for example, the display 11 and the printer 12).

Alternatively, the data of "day" and the data regarding any one or two of the items of "frequency", "calculated time", and "time difference with respect to 24 hours" may be outputted to the external devices.

The data of "calculated time" is data indicating a time corresponding to one period of the biorhythm of the test subject. The time corresponding to one period of the biorhythm of the test subject may be represented by one or both of a start time and an end time.

The data of the time waveforms exemplified in FIG. 15 may be additionally or alternatively outputted to the external devices.

As described above, it is possible to detect and determine a shift of the circadian rhythm of the test subject from the standard. Accordingly, it is possible to make use of the above determination result so as to give comment or advice on a lifestyle, sleep, and the like to the test subject, so that the circadian rhythm of the test subject approaches the normal rhythm (for example, approaches 1 Hz as practically as possible), for example.

As exemplified in FIG. 4, the biorhythm detection device 3, in parallel with the circadian rhythm calculation processing (P15), may filter the time waveform of the activity amount data (the raw data) before the frequency analysis based on the peak frequency detected in processing P14 (processing P16).

A bandpass filter (BPF) may illustratively be used for the filtering. The BPF may be, as a non-limiting example, a filter having the peak frequency, detected in processing P14, in a transmission center frequency (fc) and having a transmission band width of about ±0.25 Hz with respect to the transmission center frequency fc. The transmission center frequency fc may be variable.

By filtering the time waveform of the activity amount data with the BPF having the above transmission band characteristics, it is possible to detect the time waveform of the circadian rhythm of the test subject. For example, in the case where the time waveform of activity amount data of 24 hours a day, as exemplified in FIG. 16A, is filtered with the BPF having the above characteristics, a time waveform as exemplified in FIG. 16B is obtained.

Figure 16A:
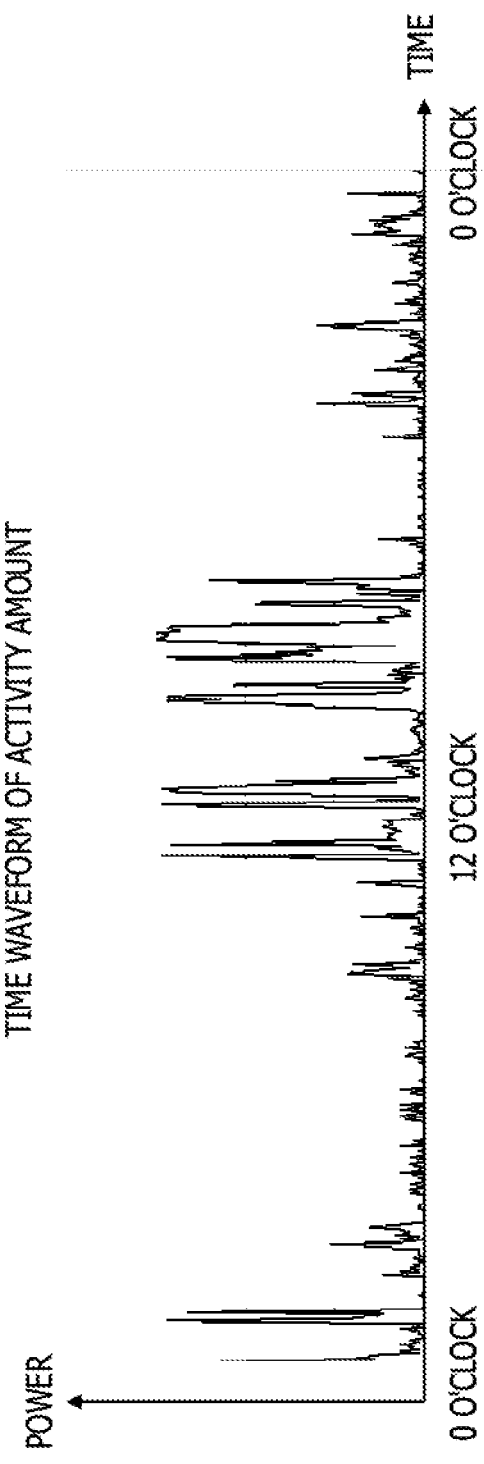
FIG. 16A is a graph illustrating an example of a time waveform of activity amount data of 24 hours.
Figure 16B:
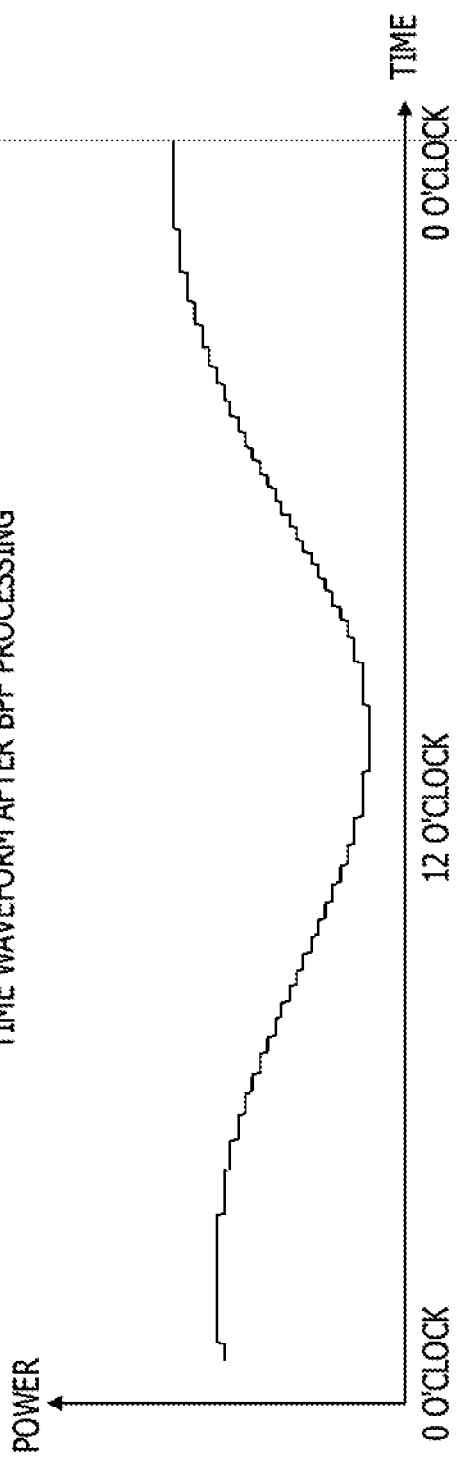
FIG. 16B is a graph illustrating an example of a time waveform obtained by filtering the time waveform of FIG. 16A using a bandpass filter (BPF).

The time waveform in FIG. 16B represents a biorhythm of one day of the test subject included in the time waveform of activity amount data in FIG. 16A, that is, represents a temporal change of a frequency component derived from the circadian rhythm.

The biorhythm detection device 3 may visually display the time waveform, as depicted in FIG. 16B, obtained by carrying out BPF processing on the activity amount data, as the circadian rhythm of the test subject (processing P17 in FIG. 4).

The visual display may illustratively be displayed on the display 11 (see FIG. 3) or printed by the printer 12 (see FIG. 3). By the circadian rhythm of the test subject being visually displayed, it becomes easy for the test subject to visually recognize the circadian rhythm of the test subject.

Figure 17:
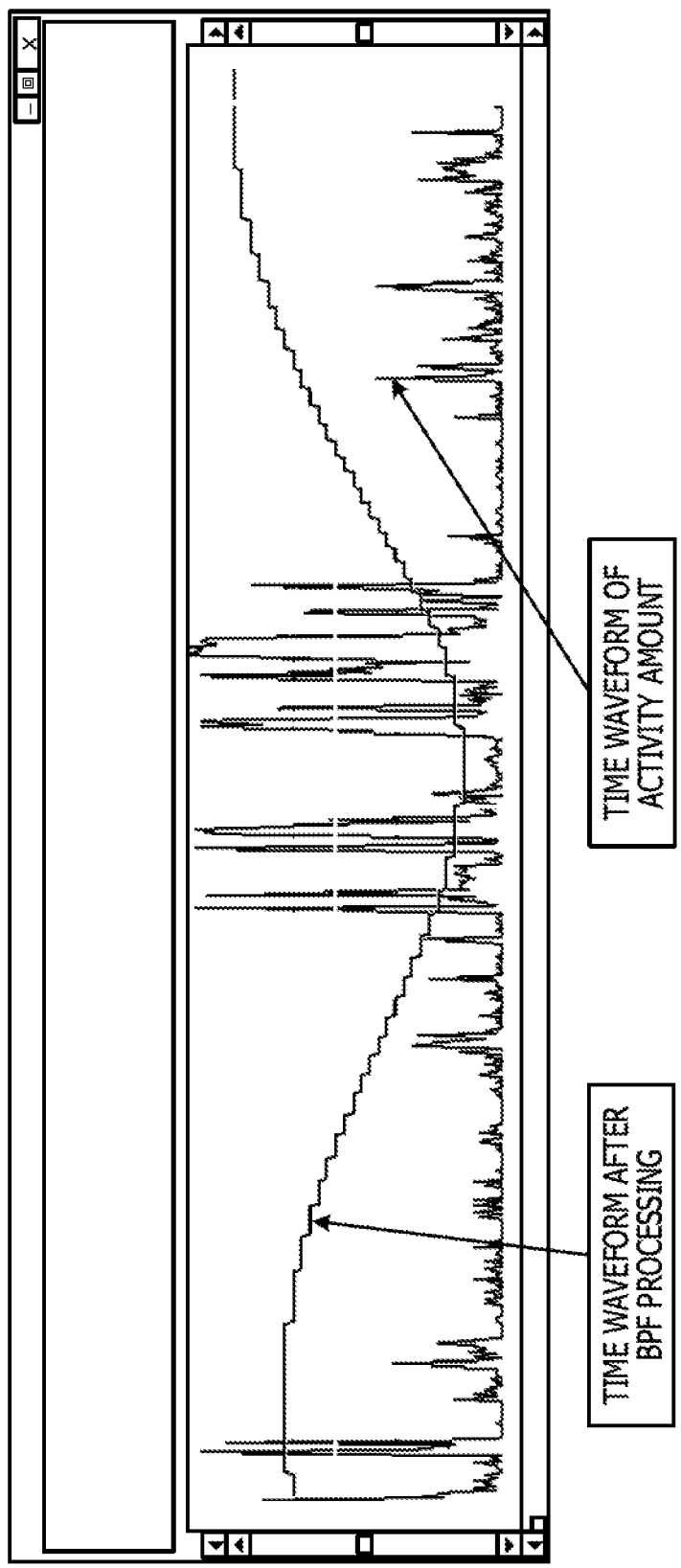
FIG. 17 is a graph illustrating an example in which the time waveforms exemplified in FIG. 16A and FIG. 16B are superimposed and displayed.

In addition, the biorhythm detection device 3 may visually display the time waveform of activity amount data as depicted in FIG. 16A, which is raw data, along with the time waveform of the circadian rhythm as depicted in FIG. 16B. In this case, the time waveform of the circadian rhythm and the time waveform of the raw data may be separately displayed, or may be displayed being superimposed as illustrated in FIG. 17, for example.

With the superimposed display, the test subject is likely to recognize easily the circadian rhythm with respect to the temporal change of the activity amount of one day of the test subject. For example, in a case where the circadian rhythm is disordered, an activity time that may be the cause of disorder in daily activities is visually and easily recognized.

Accordingly, it is easy to give, to the test subject, more appropriate and concrete comment or advice on improvements or the like related to lifestyle, sleep, and the like in accordance with real life of the test subject.

Figure 19:
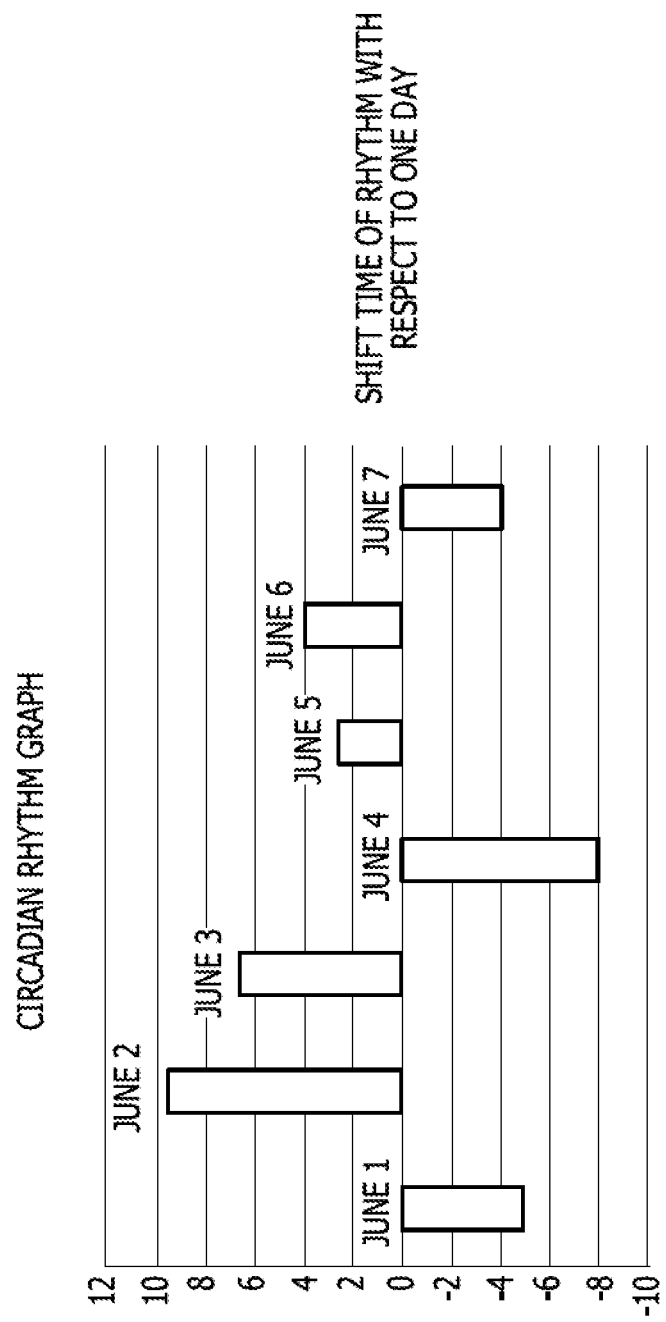
FIG. 19 is a graph illustrating an example of a visual display mode of data with regard to a circadian rhythm.
Figure 20:
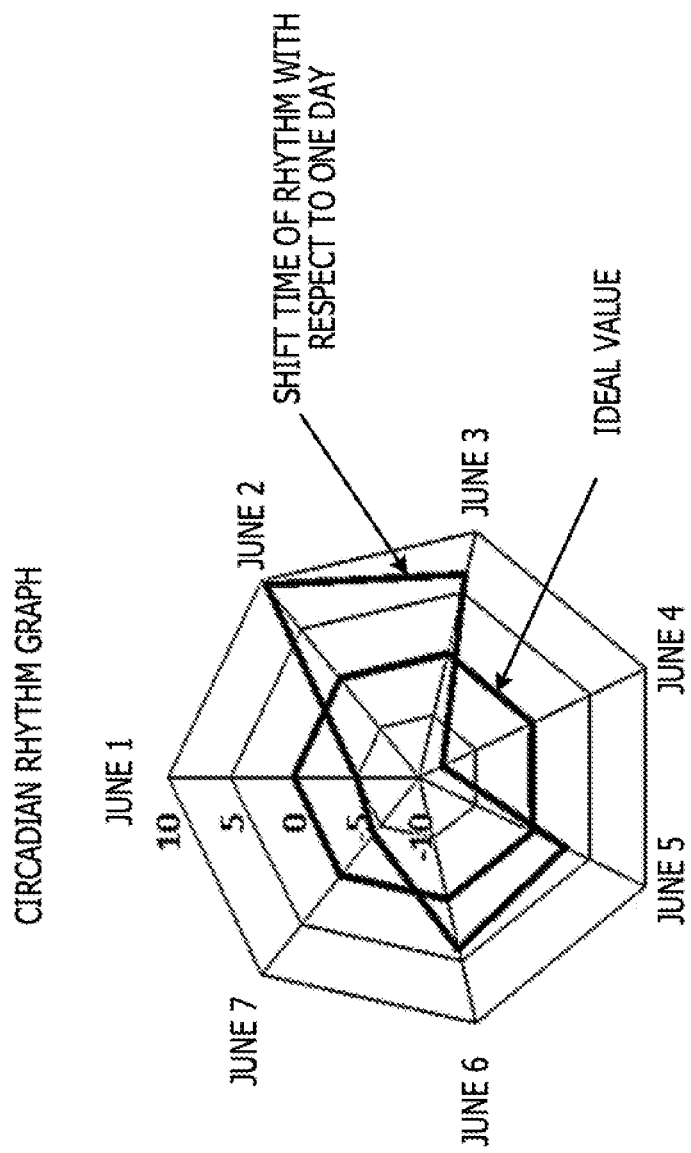
FIG. 20 is a graph illustrating an example of a visual display mode of data with regard to a circadian rhythm.

The biorhythm detection device 3 may visually display data with regard to the circadian rhythm in a display mode in which, for example, as exemplified in FIGS. 18 to 20, a shift (to rephrase, a difference) between the circadian rhythm of the test subject and the standard rhythm is likely to be recognized easily.

FIG. 18 is a table illustrating an example of a mode in which data regarding the items of "day" and "time difference with respect to 24 hours" is extracted and displayed among the items in four rows exemplified in FIG. 14. Note that in FIG. 18, part of the data (numerical values) of "time difference with respect to 24 hours" are "rounded" by rounding-off. Although visibility is improved by "rounding" the numerical values, it may not be required to "round" the numerical values.

FIG. 19 is a graph illustrating an example of a mode in which the data of seven days are graphed and displayed while the horizontal axis and the vertical axis represent the two items exemplified in FIG. 18. FIG. 20 is a graph illustrating an example of a mode in which the data of seven days are graphed and displayed while each of axes of a radar chart represent the respective two items exemplified in FIG. 18.

In the radar chart exemplified in FIG. 20, an ideal standard rhythm (ideal value) of a circadian rhythm may be displayed along with the data of the test subject. This makes it easy for the test subject to visually recognize a shift between the circadian rhythm of the test subject and the standard rhythm.

The display modes exemplified in FIGS. 18 to 20 may be appropriately combined with each other. For example, the biorhythm detection device 3 may perform visual display by combining any two or more display modes among the display modes exemplified in FIGS. 18 to 20.

Note that the display modes of data regarding the circadian rhythm are not limited to the modes exemplified in FIGS. 18 to 20. Any display mode may be employed as long as it is easy for the display mode to make the test subject recognize a shift between the circadian rhythm of the test subject and the standard rhythm. Highlighted display and less-highlighted display may be used in combination.

A target of display according to the above-mentioned various kinds of display modes is not limited to the PC 3 and the display 11 of the server 7, and may be a display of the activity amount meter 2 or a display of the mobile terminal 4.

For example, the PC 3 and the server 7 may transmit a signal for displaying the data regarding the circadian rhythm to the activity amount meter 2 and the mobile terminal 4. In the signal, not only the data regarding the circadian rhythm, but also data for controlling the above-mentioned various kinds of display modes may be included.

(Modifications)

In the above-discussed embodiment, as exemplified in FIG. 4, the circadian rhythm calculation processing (P15), and the BPF processing (P16) and the circadian rhythm display processing (P17) are carried out in parallel after the characteristic point extraction processing (P14). However, processing P15, and processing P16 and processing P17 may be individually carried out as exemplified in FIGS. 21 and 22.

Figure 21:
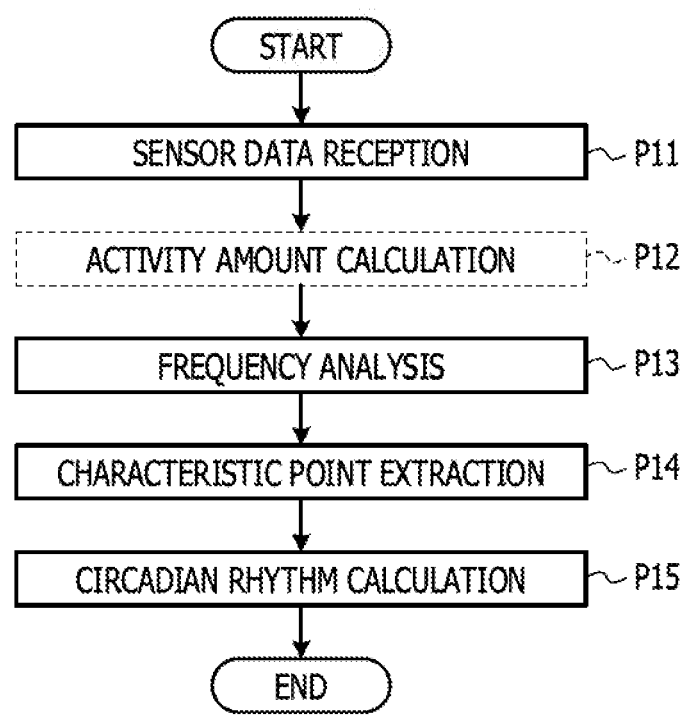
FIG. 21 is a flowchart for describing an operation example according to a modification of an embodiment.
Figure 22:
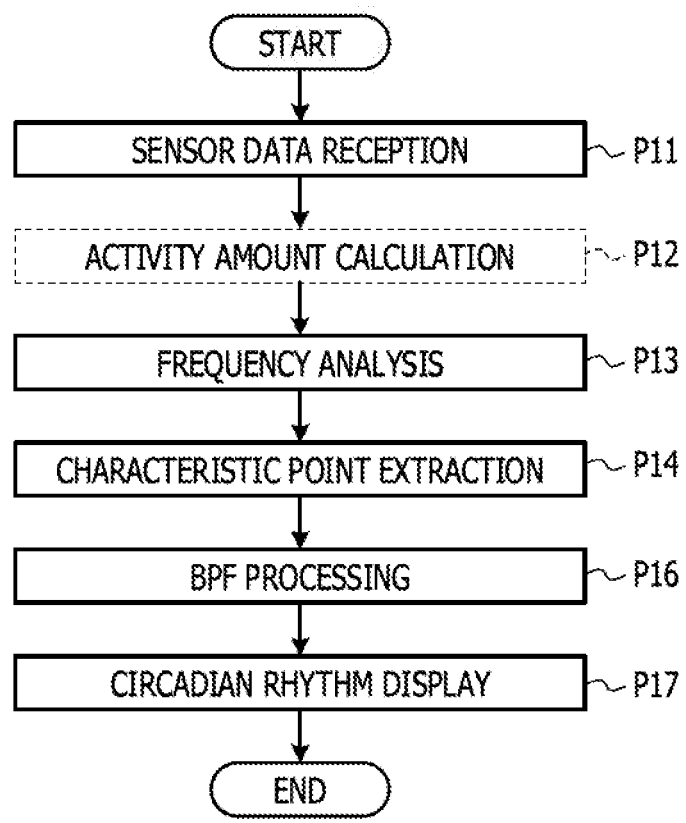
FIG. 22 is a flowchart for describing an operation example according to a modification of an embodiment.

For example, in a case where the circadian rhythm display processing is unnecessary, the biorhythm detection device 3 may carry out the above-described processing P11 to processing P15 as exemplified in FIG. 21. In a case where the circadian rhythm calculation processing is unnecessary, the biorhythm detection device 3 may carry out the above-described processing P11 to processing P14, and processing P16 and processing P17 as exemplified in FIG. 22.

Not all of the processing P11 to processing P17 may not be carried out in the PC 3 and the server 7. Part of the processing P11 to processing P17 may be carried out by the processor 22 of the activity amount meter 2 and the processor 42 of the mobile terminal 4 in accordance with the processing capacity of the processor 22 of the activity amount meter 2 and the processor 42 of the mobile terminal 4.

As discussed above, according to the above embodiments and modifications, by detecting a peak frequency, which corresponds to the characteristic point, from a result obtained through the frequency analysis of a time waveform of activity amount data of a test subject, it is possible to detect a frequency component that is derived from a biorhythm of the test subject and exhibits one cycle in a time period of approximately 24 hours.

In other words, from the time waveform of activity amount data of the test subject, components likely to be affected by the movement following the physical activities of the test subject are removed or suppressed so as to make it possible to detect the frequency component derived from the biorhythm of the test subject.

Accordingly, it is possible to detect the circadian rhythm of a test subject with ease without acquiring the blood and the rectal temperature of the test subject. Thus, it is possible to detect a shift between the circadian rhythm of the test subject and the standard rhythm, and provide comment or advice useful for improving the above shift to the test subject, which will be of assistance in health management or the like of the test subject.

For example, it is possible to give advice on a preferable wake-up time, a preferable sleep-onset time, and the like to the test subject so as to make the circadian rhythm shift be smaller. Since it is said that light is effective for controlling a circadian rhythm, it is also possible to advise the test subject to control the time of exposure to light, the time of non-exposure to light, and the like.

In addition, the activity amount meter 2 and the mobile terminal 4 may not be mounted in a mode of being restrained by the test subject in order to measure the activity amount data. For example, in a case where a sensor capable of measuring an amount of activity of the test subject without contact, such as an inertial sensor or a radio wave sensor, is applied to the activity amount sensor 21 (or 41), it is possible to measure the amount of activity in a state in which the test subject mounts the activity amount meter 2 or the mobile terminal 4 on the waist, or has it accommodated in a pocket of the clothes or the like.

In the case where a radio wave sensor is applied to the activity amount sensor 21 (or 41), even when the activity amount meter 2 or the mobile terminal 4 is placed at a location separate from the body of the test subject, it is possible to measure the amount of activity as long as the activity amount meter 2 or the mobile terminal 4 is placed within a range in which it is possible for the radio waves to reach the test subject.

Accordingly, the activity amount meter 2 and the mobile terminal 4 may not necessarily be carried by the test subject. For example, the activity amount meter 2 and the mobile terminal 4 may be placed in a room space where the test subject is positioned.

In any case, because the sensor is not required to be mounted in the mode of being restrained by the test subject (for example, the sensor is directly attached to the skin, or the like), for example, the test subject is not required to bear a physical and a psychological burden at the time of measuring the amount of activity.

Accordingly, even in a case where an amount of activity is measured for a long time, for example, 24 or more hours, it is possible to detect a circadian rhythm of the test subject with ease without obstructing the daily life of the test subject by the measurement. In other words, usability with respect to the circadian rhythm measurement may be improved.

An amount of activity of a test subject may be measured in such a manner that plural activity amount sensors 21 are temporally combined. The plurality of activity amount sensors 21 may be a combination of different types of sensors, for example, a combination of a radio wave sensor and an inertial sensor.

For example, while the test subject is at home, it is possible to measure an amount of activity of the test subject by a radio wave sensor being placed in a room; while the test subject is out of the house, it is also possible to measure the amount of activity by an inertial sensor of the activity amount meter 2 being carried by the test subject.

As a non-limiting example, it is assumed that the amount of activity is measured by the inertial sensor of the activity amount meter 2 carried by the test subject from 9 a.m. to 6 p.m., and the amount of activity is measured by the radio wave sensor placed in the room from 6 p.m. to 9 a.m. of the next morning.

In this case, the biorhythm detection device 3 may couple, in time series, the activity amount data measured by the inertial sensor during the period of time from 9 a.m. to 6 p.m. and the activity amount data measured by the radio wave sensor placed in the room during the period of time from 6 p.m. to 9 a.m. of the next morning, and then may perform the frequency analysis.

In other words, the activity amount data exemplified in FIG. 5 and FIG. 16A may be considered equivalent to the data in which pieces of activity amount data obtained by the plurality of activity amount sensors 21 are coupled in time series.

Then, the biorhythm detection device 3 assumes a single day to include just one second in a pseudo manner, and defines a one-day period to be equivalent to 1 Hz, for example, thereby making it possible to obtain a biorhythm of the test subject close to 1 Hz. The biorhythm detection device 3 may obtain a period derived from the biorhythm, from an effectual time during which the activity amount data is measured by both the activity amount sensor 21 carried by the test subject and the radio wave sensor placed in the room.

A method described in PTL 8 mentioned above, for example, may be applied to a method for obtaining activity amount data from a measurement value of the radio wave sensor. For example, changes in amplitude and frequency appear, in accordance with the magnitude and speed of the movement of the test subject, in a beat signal corresponding to the Doppler effect, which is an output signal of the radio wave sensor.

As described above, since the output signal of the radio wave sensor includes information correlated with the amount of activity of the test subject, it is possible to obtain the amount of activity (which may also be referred to as "exercise strength") of the test subject from the measurement value of the radio wave sensor.

For example, a length of a trajectory depicted in a time region by the changes in amplitude and frequency that appear in accordance with the magnitude and speed of the movement of the test subject is defined as an "extended waveform". In other words, the "extended wavelength" is equivalent to a length of a line segment obtained by linearly extending the time waveform of the measurement value of the radio wave sensor in the time region. Hence, the "extended wavelength" is a concept different from a general "wavelength".

As the amount of activity of a test subject per unit time is larger, the length of the "extended wavelength" per unit time is likely to become longer; in contrast, as the amount of activity of the test subject per unit time is smaller, the "extended wavelength" per unit time is likely to become shorter.

Accordingly, it is possible for the biorhythm detection device 3 to obtain the activity amount data of the test subject from the "extended wavelength" by converting the measurement value of the radio wave sensor into the "extended wavelength".

The "extended wavelength" may be illustratively calculated by successively storing a measurement value of the radio wave sensor in the storage section 30 (or 70) at a given period (which may be referred to as "sampling period") and adding the amounts of change in amplitude values over a unit time.

Alternatively, the "extended wavelength" may be calculated by a computing formula in which an interval of a certain curved line A-B in a time waveform, which is a measurement value of the radio wave sensor, is divided into n tiny intervals, each of the tiny intervals is approximated by a line segment, and lengths of the line segments are added.

The concept of the "extended wavelength" may be applied not only to the measurement value of the radio wave sensor, but also to measurement values of other types of sensors, such as a measurement value of an inertial sensor, a measurement value of a heartbeat sensor, a measurement value of a pulse sensor, and the like as long as these sensors are capable of measuring the amount of activity of a test subject.

(Others)

In the above embodiments and modifications, although the example in which the target of activity amount data measurement and the target of biorhythm detection are "persons" is described, the target of activity amount data measurement and the target of biorhythm detection may be applied to animals other than "persons".

For example, measuring the amount of activity of a pet animal or an animal in a zoo and detecting the biorhythm thereof with ease, will also be of assistance in health management of animals such as a pet animal or the like.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A device for biorhythm detection, comprising:
a memory; and
a processor coupled to the memory and configured to perform operations of:
    acquiring sensor data which is measured by an activity amount meter configured to measure an amount of activity of a test subject;
    calculating activity amount data indicating the amount of activity of the test subject for each time unit based on the sensor data;
    performing frequency analysis on a first time waveform of the activity amount data;
    detecting, while setting one second as the time unit and setting one Hz as a cycle of the time unit, a frequency that indicates peak power closest to the cycle of the time unit in a result which is obtained through frequency analysis as a characteristic point; and
    calculating a circadian rhythm of the test subject with setting the characteristic point as a frequency derived from a biological rhythm of the test subject.

2. The device for biorhythm detection according to claim 1, wherein the processor outputs information indicating a difference between the circadian rhythm and a standard rhythm to be a standard of the biorhythm.

3. The device for biorhythm detection according to claim 1, wherein the processor performs filtering on the first time waveform of the activity amount data with a bandpass filter having a frequency indicating the peak power in a transmission center frequency.

4. The device for biorhythm detection according to claim 3, wherein the processor outputs the first time waveform of the activity amount data and a second time waveform which is obtained by the filtering.

5. The device for biorhythm detection according to claim 4, wherein the processor outputs the first time waveform and the second time waveform to a display, and causes the display to display the first time waveform and the second time waveform being superimposed.

6. The device for biorhythm detection according to claim 1, wherein the activity amount meter includes an inertial sensor.

7. A method for biorhythm detection, the method comprising:
- acquiring, by a computer, sensor data which is measured by an activity amount meter configured to measure an amount of activity of a test subject;
- calculating activity amount data indicating the amount of activity of the test subject for each time unit based on the sensor data;
- performing frequency analysis on a first time waveform of the activity amount data;
- detecting, while setting one second as the time unit and setting one Hz as a cycle of the time unit, a frequency that indicates peak power closest to the cycle of the time unit in a result which is obtained through frequency analysis as a characteristic point; and
- calculating a circadian rhythm of the test subject with setting the characteristic point as a frequency derived from a biological rhythm of the test subject.

8. The method for biorhythm detection according to claim 7, further comprising: outputting information indicating a difference between the circadian rhythm and a standard rhythm to be a standard of the biorhythm.

9. The method for biorhythm detection according to claim 7, further comprising: performing filtering on the first time waveform of the activity amount data with a bandpass filter having a frequency indicating the peak power in a transmission center frequency.

10. The method for biorhythm detection according to claim 9, further comprising: outputting the first time waveform of the activity amount data and a second time waveform which is obtained by the filtering.

11. The method for biorhythm detection according to claim 10, further comprising: outputting the first time waveform and the second time waveform to a display, and causes the display to display the first time waveform and the second time waveform being superimposed.

12. The method for biorhythm detection according to claim 7, wherein the activity amount meter includes an inertial sensor.

13. A non-transitory computer-readable recording medium recording a program for biorhythm detection that causes a computer to execute a process, the process comprising:
- acquiring sensor data which is measured by an activity amount meter configured to measure the amount of activity of the test subject;
- calculating activity amount data indicating the amount of activity of the test subject for each time unit based on the sensor data;
- performing frequency analysis on a first time waveform of the activity amount data;
- detecting, while setting one second as the time unit and setting one Hz as a cycle of the time unit, a frequency that indicates peak power closest to the cycle of the time unit in a result which is obtained through frequency analysis as a characteristic point; and
- calculating a circadian rhythm of the test subject with setting the characteristic point as a frequency derived from a biological rhythm of the test subject.

14. The non-transitory computer-readable recording medium according to claim 13, further comprising:
- outputting information indicating a difference between the circadian rhythm and a standard rhythm to be a standard of the biorhythm.

15. The non-transitory computer-readable recording medium according to claim 13, further comprising: performing filtering on the first time waveform of the activity amount data with a bandpass filter having a frequency indicating the peak power in a transmission center frequency.

16. The non-transitory computer-readable recording medium according to claim 15, further comprising: outputting the first time waveform of the activity amount data and a second time waveform which is obtained by the filtering.

17. The non-transitory computer-readable recording medium according to claim 16 further comprising: outputting the first time waveform and the second time waveform to a display, and causes the display to display the first time waveform and the second time waveform being superimposed.

* * * * *